United States Patent
Manley et al.

(10) Patent No.: US 6,624,174 B2
(45) Date of Patent: Sep. 23, 2003

(54) 2-AMINO-NICOTINAMIDE DERIVATIVES AND THEIR USE AS VEGF-RECEPTOR TYROSINE KINASE INHIBITORS

(75) Inventors: Paul William Manley, Arlesheim (CH); Guido Bold, Gipf-Oberfrick (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 10/181,005

(22) PCT Filed: Jan. 25, 2001

(86) PCT No.: PCT/EP01/00835
§ 371 (c)(1),
(2), (4) Date: Jul. 11, 2002

(87) PCT Pub. No.: WO01/55114
PCT Pub. Date: Aug. 2, 2001

(65) Prior Publication Data
US 2003/0032656 A1 Feb. 13, 2003

(30) Foreign Application Priority Data
Jan. 27, 2000 (GB) .............................................. 0001930

(51) Int. Cl.[7] .................... C07D 213/82; C07D 401/02; A61K 31/47; A61K 31/44
(52) U.S. Cl. ........................ 514/310; 514/352; 546/143; 546/309
(58) Field of Search ................... 546/307.143; 514/352, 514/310

(56) References Cited

FOREIGN PATENT DOCUMENTS

| EP | 0 393 529 | 10/1990 |
|----|-----------|---------|
| WO | WO 98/07726 | 2/1998 |
| WO | WO 98/45268 | 10/1998 |
| WO | WO 98/57957 | 12/1998 |
| WO | WO 99/20606 | 4/1999 |
| WO | WO 99/62885 | 12/1999 |
| WO | WO 00/39111 | 7/2000 |
| WO | WO 00/62778 | 10/2000 |
| WO | WO 01/55115 | 8/2001 |

OTHER PUBLICATIONS

Zhumrenko et al., "Synthesis and Pharmacological Properties of 2–Aminonicotinamide Derivatives", Fiziol. Akt. Veshchestva, vol. 8, pp. 89–94 (1976)—[Abstract 86: 171214 CA].

Akhundov et al., "Synthesis and Psychotropic Activity of Amides of 2–Aminonicotinic Acid", Khim.–Farm. Zh., vol. 20, No. 1, pp. 32–35 (1986).

*Primary Examiner*—Zinna Northington Davis
(74) *Attorney, Agent, or Firm*—George R. Dohmann

(57) ABSTRACT

The invention relates to the use of 2 amino-nicotinamide derivatives of formula I

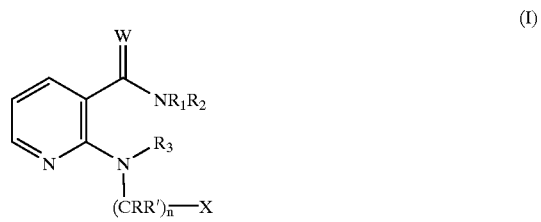

(I)

wherein n is from 1 up to and including 6;
W is O or S;
$R_1$ and $R_3$ represent independently of each other hydrogen, lower alkyl or lower acyl;
$R_2$ represents a cycloalkyl group, an aryl group, or a mono- or bicyclic heteroaryl group comprising one or more ring nitrogen atoms and 0, 1 or 2 heteroatoms independently from each other selected from the group consisting of oxygen and sulfur, which groups in each case are unsubstituted or mono- or polysubstituted;
R and R' are independently of each other hydrogen or lower alkyl;
X represents an aryl group, or a mono- or bicyclic heteroaryl group comprising one or more ring nitrogen atoms and 0, 1 or 2 heteroatoms independently from each other selected from the group consisting of oxygen and sulfur, which groups in each case are unsubstituted or mono- or polysubstituted;
or a N-oxide, a possible tautomer thereof or a pharmaceutically acceptable salt of such a compound, alone or in combination with one or more other pharmaceutically active compounds for the preparation of a pharmaceutical composition for use for therapy of a disease which responds to an inhibition of the VEGF-receptor tyrosine kinase activity;
and to new 2-amino-nicotinamide derivatives of formula I and processes for the preparation thereof.

15 Claims, No Drawings

2-AMINO-NICOTINAMIDE DERIVATIVES AND THEIR USE AS VEGF-RECEPTOR TYROSINE KINASE INHIBITORS

This application is a 371 of PCT/EP01/00835 filed Jan. 25, 2001.

The invention relates to the use of 2-amino-nicotinamide derivatives alone or in combination with one or more other pharmaceutically active compounds for the preparation of a pharmaceutical composition for use for therapy of a disease which responds to an inhibition of the VEGF-receptor tyrosine kinase activity, especially a neoplastic disease, retinopathy or age-related macular degeneration; a method for the treatment of such a disease in animals, especially in humans; new 2-amino-nicotinamide derivatives and processes for the preparation thereof.

Certain diseases are known to be associated with deregulated angiogenesis, for example diseases caused by ocular neovascularisation, such as retinopathies (including diabetic retinopathy), age-related macular degeneration, psoriasis, haemangioblastoma, haeman-gioma, endometriosis, and especially neoplastic diseases, for example so-called solid tumors and liquid tumors (such as leukemias).

According to recent findings, at the centre of the network regulating the growth and differentiation of the vascular system and its components, both during embryonic development and normal growth and in a wide number of pathological anomalies and diseases, lies the angiogenic factor known as "Vascular Endothelial Growth Factor" (=VGEF; originally termed "Vascular Permeability Factor",=VPF), along with its cellular receptors (see Breler, G., et al., Trends in Cell Biology 6, 454–6 [1996] and references cited therein).

VEGF is a dimerc, disulfide-linked 46-kDa glycoprotein produced by normal cell lines and tumor cell lines. It is an endothelial cell-specific mitogen, shows angiogenic activity in in vivo test systems (e.g. rabbit cornea), is chemotactic for endothelial cells and monocytes, and induces plasminogen activators in endothelial cells, which are then involved in the proteolytc degradation of extracellular matrix during the formation of capillaries. A number of isoforms of VEGF are known, which show comparable biological activity, but differ in the type of cells that secrete them and in their heparin-binding capacity. In addition, there are other members of the VEGF family, such as "Placenta Growth Factor" (PLGF) and VEGF-C.

VEGF receptors are transmembranous receptor tyrosine kinases. They are characterized by an extracellular domain with seven immunoglobulin-like domains and an intracellular tyrosine kinase domain. Various types of VEGF receptor are known, e.g. VEGFR-1, VEGFR-2, and VEGFR-3.

A large number of human tumors, especially gliomas and carcinomas, express high levels of VEGF and its receptors. This has led to the hypothesis that the VEGF released by tumor cells could stimulate the growth of blood capillaries and the proliferation of tumor endothelium in a paracrine manner and thus, through the improved blood supply, accelerate tumor growth. Increased VEGF expression could explain the occurrence of cerebral oedema in patients with glioma. Direct evidence of the role of VEGF as a tumor angiogenesis factor in vivo has been obtained from studies in which VEGF expression or VEGF activity was inhibited. This was achieved with antibodies which inhibit VEGF activity, with dominant-negative VEGFR-2 mutants which inhibited signal transduction, or with the use of antisense-VEGF RNA techniques. All approaches led to a reduction in the growth of glioma cell lines or other tumor cell lines in vivo as a result of inhibited tumor angiogenesis.

Angiogenesis is regarded as an absolute prerequisite for those tumors which grow beyond a maximum diameter of about 1–2 mm; up to this limit, oxygen and nutrients may be supplied to the tumor cells by diffusion. Every tumor, regardless of its origin and its cause, is thus dependent on angiogenesis for its growth after it has reached a certain size.

Three principal mechanisms play an important part in the activity of angiogenesis inhibitors against tumors: 1) Inhibition of the growth of vessels, especially capillaries, into a vascular resting tumors, with the result that there is no net tumor growth owing to the balance that is achieved between apoptosis and proliferation; 2) Prevention of the migration of tumor cells owing to the absence of blood flow to and from tumors; and 3) Inhibition of endothelial cell proliferation, thus avoiding the paracrine growth-stimulating effect exerted on the surrounding tissue by the endothelial cells which normally line the vessels.

Surprisingly, it has now been found that nicotinamide derivatives of formula I, described below, are a new class of compounds that have advantageous pharmacological properties and inhibit, for example, the activity of the VEGF receptor tyrosine kinase, the growth of tumors and VEGF-dependent cell proliferation, and the other diseases mentioned above and below.

The compounds of formula I open up, for example, an unexpected new therapeutic approach, especially for diseases in the treatment of which, and also for the prevention of which, an inhibition of angiogenesis and/or of the VEGF receptor tyrosine kinase shows beneficial effects.

The invention relates to the use of a compound of formula I,

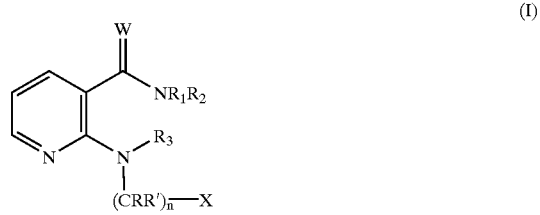

(I)

wherein
n is from 1 up to and including 6;
W is O or S;
$R_1$ and $R_3$ represent independently of each other hydrogen, lower alkyl or lower acyl;
$R_2$ represents an cycloalkyl group, an aryl group, or a mono- or bicyclic heteroaryl group comprising one or more ring nitrogen atoms and 0, 1 or 2 heteroatoms independently from each other selected from the group consisting of oxygen and sulfur, which groups in each case are unsubstituted or mono- or polysubstituted;
R and R' are independently of each other hydrogen or lower alkyl;
X represents an aryl group, or a mono- or bicyclic heteroaryl group comprising one or more ring nitrogen atoms and 0, 1 or 2 heteroatoms independently from each other selected from the group consisting of oxygen and sulfur, which groups in each case are unsubstituted or mono- or polysubstituted;
and of a N-oxide or a possible tautomer thereof;
or of a pharmaceutically acceptable salt of such a compound for the preparation of a pharmaceutical composition for the treatment of a disease which responds to an inhibition of the VEGF receptor tyrosine kinase activity.

The general terms used hereinbefore and hereinafter preferably,have within the context of this disclosure the following meanings, unless otherwise indicated:

The prefix "lower" denotes a radical having up to and including a maximum of 7, especially up to and including a maximum of 4 carbon atoms, the radicals in question being either linear or branched with single or multiple branching.

Where the plural form is used for compounds, salts, and the like, this is taken to mean also a single compound, salt, or the like.

Any asymmetric carbon atoms (for example in compounds of formula I, wherein R or R' is lower alkyl) may be present in the (R)-, (S)- or (R,S)-configuration, preferably in the (R)- or (S)-configuration. The compounds may thus be present as mixtures of isomers or as pure isomers, preferably as enantiomer-pure diastereomers.

The invention relates also to possible tautomers of the compounds of formula I.

X is preferably pyridyl or phenyl, most preferred it is 3- or 4-pyridyl.

In a preferred embodiment of the invention X is substituted by lower alkoxy.

In further a very preferred embodiment of the invention X has the substructure X'

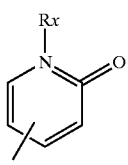

(X')

wherein Rx is hydrogen or lower alkyl.

$R_2$ is preferably phenyl which is mono- or disubstituted by lower alkyl, lower alkynyl, halogen, preferably fluoro, and trifluorbmethyl; or cycloalkyl, preferably cydohexyl substituted by lower alkyl, preferably tert-butyl.

$R_3$ is preferably hydrogen.

W is preferably O.

The integer n is preferably 1 or 2, very preferably 1.

Lower alkyl is preferably alkyl with from and including 1 up to and including 7, preferably from and including 1 to and including 5, and is linear or branched; preferably, lower alkyl is pentyl, such as n-pentyl, butyl, such as n-butyl, sec-butyl, isobutyl, tert-butyl, propyl, such as n-propyl or isopropyl, ethyl or methyl. Preferably lower alkyl is methyl, propyl or tert-butyl.

Lower acyl is preferably formyl or acetyl.

"Aryl" is an aromatic radical which is bound to the molecule via a bond located at an aromatic ring carbon atom of the radical. In a preferred embodiment, aryl is an aromatic radical having 6 to 14 carbon atoms, especially phenyl, naphthyl, tetrahydronaphthyl, fluorenyl or phenanthrenyl, and is unsubstituted or substituted by one or more, preferably up to three, especially one or two substituents, especially selected from amino, mono- or disubstituted amino, halogen, lower alkyl, substituted alkyl, lower alkenyl, lower alkynyl, lower alkanoyl, hydroxy, etherified or esterified hydroxy, nitro, cyano, carboxy, esterified carboxy, alkanoyl, berizoyl, carbamoyl, N-mono or N,N-disubstituted carbamoyl, amidino, guanidino, ureido, mercapto, sulfo, lower alkylthio, phenyl, phenoxy, phenylthio, phenyl-lower alkylthio, alkylphenylthio, lower alkylsulfinyl, phenylsulfinyl, phenyl-lower alkylsulfinyl, alkylphenylsulfinyl, lower alkanesulfonyl, phenylsulfonyl, phenyl-lower alkylsulfonyl, alkylphenylsulfonyl, halogen-lower alkylmercapto, halogen-lower alkylsulfonyl, such as especially trifluoromethane sulfonyl, dihydroxybora (—B(OH)$_2$), heterocyclyl, and lower alkylene dioxy bound at adjacent C-atoms of the ring, such as methylene dioxy. Aryl is more preferably phenyl or naphthyl, which in each case is either unsubstituted or independently substituted by one or two substituents selected from the group comprising halogen, especially fluorine, chlorine, or bromine; hydroxy; hydroxy, etherified by lower alkyl, e.g. methyl or by halogen-lower alkyl, e.g. trifluoromethyl; lower alkyl, e.g. methyl or propyl; lower alkynyl, such as 1-propynyl; esterified carboxy, especially lower alkoxy carbonyl, e.g. methoxy carbonyl, n-propoxy carbonyl or iso-propoxy carbonyl; N-mono-substituted carbamoyl, in particular carbamoyl monosubstituted by lower alkyl, e.g. methyl, n-propyl or iso-propyl; substituted alkyl, especially lower alkyl, e.g. methyl or ethyl, substituted by lower alkoxy carbonyl, e.g. methoxy carbonyl or ethoxy carbonyl; and halogen-lower alkyl, most preferably trifluoromethyl.

Aryl in the form of phenyl which is substituted by lower alkylene dioxy bound to two adjacent C-atoms, such as methylenedioxy, is preferably 3,4-methylenedioxyphenyl.

A cycloalkyl group is preferably cyclopentyl, cyclohexyl or cycloheptyl, and maybe unsubstitutedor substituted by one or more, especially one or two, substitutents selected from the group defined above as substitutents for aryl, most preferably by lower alkyl, such as methyl, lower alkoxy, such as methoxy or ethoxy, or hydroxy.

Substituted alkyl is alkyl as last defined, especially lower alkyl, preferably methyl; where one or more, especially up to three, substituents may be present, primarily from the group selected from halogen, especially fluorine, amino, N-lower alkylamino, N,N-di-lower alkylamino, N-lower alkanoylamino, hydroxy, cyano, carboxy, lower alkoxycarbonyl, and phenyl-lower alkoxycarbbnyl. Trifluoromethyl is especially preferred.

Mono- or disubstituted amino is especially amino substituted by one or two radicals selected independently of one another from lower alkyl, such as methyl; hydroxy-lower alkyl, such as 2-hydroxyethyl; phenyl-lower alkyl; lower alkanoyl, such as acetyl; benzoyl; substituted benzoyl, wherein the phenyl radical is especially substituted by one or more, preferably one or two, substituents selected from nitro, amino, halogen, N-lower alkylamino, N,N-di-lower alkylamino, hydroxy, cyano, carboxy, lower alkoxycarbonyl, lower alkanoyl, and carbamoyl; and phenyl-lower alkoxycarbonyl, wherein the phenyl radical is unsubstituted or especially substituted by one or more, preferably one or two, substituents selected from nitro, amino, halogen, N-lower alkylamino, N,N-di-lower alkylamino, hydroxy, cyano, carboxy, lower alkoxycarbonyl, lower alkanoyl, and carbamoyl; and is preferably N-lower alkylamino, such as N-methylamino, hydroxy-lower alkylamino, such as 2-hydroxyethylamino, phenyl-lower alkylamino, such as benzylamino, N,N-di-lower-alkylamino, N-phenyl-lower alkyl N-lower alkylamino, N,N-di-lower alkylphenylamino, lower alkanoylamino, such as acetylamino, or a substituent selected from the group comprising benzoylamino and phenyl-lower alkoxycarbonyl-amino, wherein the phenyl radical In each case is unsubstituted or especially substituted by nitro or amino, or also by halogen, amino, N-lower alkylamino, N,N-di-lower alkylamino, hydroxy, cyano, carboxy, lower alkoxycarbonyl, lower alkanoyl, carbamoyl or aminocarbonylamino.

Halogen is especially fluorine, chlorine, bromine, or iodine, especially fluorine, chlorine, or bromine.

Etherified hydroxy is especially $C_8$–$C_{20}$alkyloxy, such as n-decyloxy, lower alkoxy (preferred), such as methoxy, ethoxy, isopropyloxy, or n-pentyloxy, phenyl-lower alkoxy, such as benzyloxy, or also phenyloxy, or as an alternative or in addition to the previous group $C_1$–$C_{20}$alkyloxy, such as ndecyloxy, halogen-lower alkoxy, such as trifluoromethyloxy or 1,1,2,2-tetrafluoroethoxy.

Esterified hydroxy is especially lower alkanoyloxy, benzoyloxy, lower alkoxycarbonyloxy, such as tert-butoxycarbonyloxy, or phenyl-lower alkoxycarbonyloxy, such as benzyloxycarbonyloxy.

Esterified carboxy is especially lower alkoxycarbonyl, such as tert-butoxycarbonyl, isopropoxycarbonyl, methoxycarbonyl or ethoxycarbonyl, phenyl-lower alkoxycarbonyl, or phenyloxycarbonyl.

Alkanoyl is primarily alkylcarbonyl, especially lower alkanoyl, e.g. acetyl.

N-Mono- or N,N-disubstituted carbamoyl is especially subsfftuted by one or two substituents independently selected from lower alkyl, phenyl-lower alkyl, and hydroxy-lower alkyl, at the terminal nitrogen atom.

Alkylphenytthio is especially lower alkylphenylthio.

Alkylphenylsulfonyl is especially lower alkylphenylsulfonyl.

Alkylphenylsulfinyl Is especially lower alkylphenylsulfinyl.

A mono- or bicyclic heteroaryl group comprising one or more ring nitrogen atoms and 0, 1 or 2 heteroatoms independently from each other selected from the group consisting of oxygen and sulfur, which groups in each case are unsubstituted or mono- or polysubstituted refers to a heterocyclic moiety that is unsaturated in the ring binding the heteroaryl radical to the rest of the molecule in formula I and is preferably a ring, where at least in the binding ring, but optionally also in any annealed ring, one or more, preferably 1 to 4, most preferably 1 or 2, carbon atoms are replaced each by a heteroatom selected from the group consisting of nitrogen, oxygen and sulfur; where the binding ring preferably has 5 to 12, more preferably 5 to 7 ring atoms; and may be unsubstituted or substituted by one or more, especially one or two, substitutents selected from the group defined above as substitutents for aryl, most preferably by lower alkyl, such as methyl, lower alkoxy, such as methoxy or ethoxy, or hydroxy; preferably the mono- or bicyclic heteroaryl group is selected from 2H-pyrrolyl, pyrrolyl, imidazolyl, benzimidazolyl, pyrazolyl, indazolyl, purinyl, pyridyl, pyrazinyl, pyrimidinyl, pyridazinyl, 4H-quinolizinyl, isoquinolyi, quinolyl, phthalazinyl, naphthyridinyl, quinoxalyl, quinazolinyl, quinnolinyl, pteridinyl, indolizinyl, 3H-indolyl, indolyl, isoindolyl, oxazolyl, isoxazolyl, thiazolyl, isothiazolyl, triazolyl, tetrazolyl, furazanyl and benzo[d]pyrazol. More preferably the mono- or bicyclic heteroaryl group is selected from the group consisting of pyrrolyl, benzimidazolyl, such as 1-benzimidazolyl, indazolyl, especially 5-indazolyl, pyridyl, especially 2-, 3- or 4-pyridyl, isoquinolinyl, especially 3-isoquinolinyl, quinolinyl, especially 4-quinolinyl, indolyl, especially 3-indolyl, thiazolyl, or benzo[d]pyrazol. In one preferred embodiment of the invention the pyridyl radical is substituted by hydroxy in ortho position to the nitrogen atom and hence exists at least partially in the form of the corresponding tautomer which is pyridin-(1H)2-one.

Heterocyclyl is especially a five or six-membered heterocyclic system with 1 or 2 heteroatoms selected from the group comprising nitrogen, oxygen, and sulfur, which may be unsaturated or wholly or partly saturated, and is unsubstituted or substituted especially by lower alkyl, such as methyl; a radical selected from 2-methylpyrimidin-4-yl, oxazol-5-yl, 2-methyl-1,3-dioxolan-2-yl, 1H-pyrazol-3-yl, and 1-methyl-pyrazol-3-yl is preferred.

Salts are especially the pharmaceutically acceptable salts of compounds of formula I.

Such salts are formed, for example, as acid addition salts, preferably with organic or inorganic acids, from compounds of formula I with a basic nitrogen atom, especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, tumaric acid, succinic acid, adipic acid, pimelic acid, suberic acid, azelaic acid, malic acid, tartaric acid, citric acid, anino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethanesulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3- or 4-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

In the presence of negatively charged radicals, such as carboxy or sulfo, salts may also be formed with bases, e.g. metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethyl-piperidine or N,N'-dimethylpiperazine.

When a basic group and an acid group are present in the same molecule, a compound of formula I may also form internal salts.

For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred.

In view of the close relationship between the novel compounds in free form and those in the form of their salts, including those salts that can be used as intermediates, for example in the purification or identification of the novel compounds, any reference to the free compounds hereinbefore and hereinafter is to be understood as referring also to the corresponding salts, as appropriate and expedient.

The compounds of formula I and N-oxides thereof have valuable pharmacological properties, as described hereinbefore and hereinafter.

The efficacy of the compounds of the invention as inhibitors of VEGF-receptor tyrosine kinase activity can be demonstrated as follows:

Test for activity against VEGF-receptor tyrosine kinase. The test is conducted using Flt-1 VEGF-receptor tyrosine kinase. The detailed procedure is as follows: 30 $\mu$l kinase solution (10 $\mu$g of the kinase domain of Flt-1, Shibuya et al., Oncogene 5, 519–24 [1990]) in 20 mM Tris.HCl pH 7.5, 3 mM manganese dichloride ($MnCl_2$), 3 mM magnesium chloride ($MgCl_2$), 10 $\mu$M sodium vanadate, 0.25 mg/ml polyethylenglycol (PEG) 20000, 1 mM dithiothreitol and 3 $\mu l/\mu l$ poly(Glu,Tyr) 4:1 (Sigma, Buchs, Switzerland), 8 $\mu M$ [$^{33}P$]-ATP (0.2 $\mu Ci$), 1% dimethyl sulfoxide, and 0 to 100 $\mu M$ of the compound to be tested are incubated together for 10 minutes at room temperature. The reaction is then terminated by the addition of 10 $\mu l$ 0.25 M ethylenediaminetetraacetate (EDTA) pH 7. Using a multichannel dispenser (LAB SYSTEMS, USA), an aliquot of 20 $\mu l$ is applied to a PVDF (=polyvinyl difluoride) Immobilon P membrane (Millipore, USA), through a Gibco-BRL microtiter filter manifold and connected to a vacuum. Following complete elimination of the liquid, the membrane is washed 4 times successively in a bath containing 0.5% phosphoric acid ($H_3PO_4$) and once with ethanol, incubated for 10 minutes each time while shaking, then mounted in a Hewlett Packard TopCount Manifold and the radioactivity measured after the addition of 10 $\mu l$ Microscint® ($\beta$-scintilation counter liquid). $IC_{50}$-values are determined by linear regression analysis of the percentages for the inhibition of each compound in three concentrations (as a rule 0.01, 0.1, and 1 mmol). The $IC_{50}$-values that can be found with compounds of formula I are in the range of 1 to 1000 nM, preferably in the range of 1 to 100 nM.

The antitumor efficacy of the compounds of the invention can be demonstrated in vivo as follows:

In vivo activity in the nude mouse xenotransplant model: female BALB/c nude mice (8–12 weeks old), Novartis Animal Farm, Sisseln, Switzerland) are kept under sterile conditions with water and feed ad libitum. Tumors are induced either by subcutaneous injection of tumor cells into mice (for example, Du 145 prostate carcinoma cell line (ATCC No. HTB 81; see Cancer Research 37, 4049–58 (1978)) or by implanting tumor fragments (about 25 mg) subcutaneously into the left flank of mice using a 13-gauge trocar needle under Forene® anaesthesia (Abbott, Switzerland). Treatment with the test compound is started as soon as the tumor has reached a mean volume of 100 $mm^3$. Tumor growth is measured two to three times a week and 24 hours after the last treatment by determining the length of two perpendicular axes. The tumor volumes are calculated in accordance with published methods (see Evans et al., Brit. J. Cancer 45, 466–8 [1982]). The antitumor efficacy is determined as the mean increase in tumor volume of the treated animals divided by the mean increase in tumor volume of the untreated animals (controls) and, after multiplication by 100, is expressed as T/C%. Tumor regression (given in %) is reported as the smallest mean tumor volume in relation to the mean tumor volume at the start of treatment. The test compound is administered daily by gavage.

As an alternative other cell lines may also be used in the same manner, for example:

the MCF-7 breast adenocarcinoma cell line (ATCC No. HTB 22; see also J. Nati. Cancer Inst. (Bethesda) 51, 1409–16 [1973]);

the MDA-MB 468 breast adenocarcinoma cell line (ATCC No. HTB 132; see also In Vitro 14, 911–15 [1978]);

the MDA-MB 231 breast adenocarcinoma cell line (ATCC No. HTB 26; see also J. Natl. Cancer Inst. (Bethesda) 53, 661–74 [1974]);

the Colo 205 colon carcinoma cell line (ATCC No. CCL 222; see also Cancer Res. 38, 1345–55 [1978]);

the HCT 116 colon carcinoma cell line (ATCC No. CCL 247; see also Cancer Res. 41, 1751–6 [1981]);

the DU145 prostate carcinoma cell line DU145 (ATCC No. HTB 81; see also Cancer Res. 37, 4049–58 [1978]); and the PC3 prostate carcinoma cell line PC-3 (ATCC No. CRL 1435; see also Cancer Res. 40, 524–34 [1980]).

The inhibition of VEGF-induced KDR-receptor autophosphorylation can be confirmed with a further in vitro experiment in cells: transfected CHO cells, which permanently express human VEGF receptor (KDR), are seeded in complete culture medium (with 10% fetal calf seum=FCS) in 6-well cell-culture plates and incubated at 37° C. under 5% $CO_2$ until they show about 80% confluency. The compounds to.be tested are then diluted in culture medium (without FCS, with 0.1% bovine serum albumin) and added to the cells. (Controls comprise medium without test compounds). After two hours of incubation at 37° C., recombinant VEGF is added; the final VEGF concentration is 20 ng/ml). After a further five minute incubation at 37° C., the cells are washed twice with ice-cold PBS (phosphate-buffered saline) and immediately lysed in 100 $\mu l$ lysis buffer per well. The lysates are then centrifuged to remove the cell nuclei, and the protein concentrations of the supematants are determined using a commercial protein assay (BIORAD). The lysates can then either be immediately used or, if necessary, stored at −20° C.

A sandwich ELISA is carried out to measure the KDR-receptor phosphorylation: a monoclonal antibody to KDR (for example Mab 1495.12.14; prepared by H. Towbin) is immobilized on black ELISA plates (OptiPlate™ HTRF-96 from Packard). The plates are then washed and the remaining free protein-binding sites are saturated with 1% BSA in PBS. The cell lysates (20 $\mu g$ protein per well) are then incubated in these plates overnight at 4° C. together with an antiphosphotyrosine antibody coupled with alkaline phosphatase (PY20:AP from Transduction Laboratories). The (plates are washed again and the) binding of the antiphosphotyrosine antibody to the captured phosphorylated receptor is then demonstrated using a luminescent AP substrate (CDPStar, ready to use, with Emerald 11; TROPIX). The luminescence is measured in a Packard Top Count Microplate Scintillation Counter Cop Count). The difference between the signal of the positive control (stimulated with VEGF) and that of the negative control (not stimulated with VEGF) corresponds to VEGFnduced KDR-receptor phosphorylation (=100%). The activity of the tested substances is calculated as % inhibition of VEGFnduced KDR-receptor phosphorylaton, wherein the concentration of substance that induces half the maximum inhibition is defined as the ED50 (effective dose for 50% inhibition). Compounds of formula I here preferably show ED50 values in the range of 0.25 nM to 1000 nM, preferably 0.25 to 250 nM.

A compound of formula I or a N-oxide thereof inhibits to varying degrees also other tyrosine kinases involved in signal transduction which are mediated by trophic factors, for example AbI kinase, kinases from the Src family, especially c-Src kinase, Lck, and Fyn; also kinases of the EGF family, for example, c-erbB2 kinase (HER-2), c-erbB3 kinase, c-erbB4 kinase; insulin-like growth factor receptor kinase (IGF-1 kinase), especially members of the PDGF-receptor tyrosine kinase family, such as PDGF-receptor kinase, CSF-1-receptor kinase, Kit-receptor kinase and VEGF-receptor kinase; and also serine/threonine kinases, all of which play a role in growth regulation and transformation in mammalian cells, including human cells.

The inhibition of c-erbB2 tyrosine kinase (HER-2) can be measured, for example, In the same way as the inhibition of EGF-R protein kinase (see House et al., Europ. J. Biochem. 140, 363–7 [1984]). The erbB2 kinase can be isolated, and its activity determined, using methods known per se (see T. Akiyama et al., Science 232, 1644 [1986]).

On the basis of these studies, a compound of formula I according to the invention shows therapeutic efficacy especially against disorders dependent on protein kinase, especially proliferative diseases.

The activity of compounds of the formula I against pain can be shown in the following model of nocicepton (pain). In this model, the hyperalgesia caused by an intralanar yeast injection is measured by applying increased pressure to the foot until the animal vocalizes or withdraws its foot from the applied pressure pad. The model is sensitive to COX inhibitors, and diclofenac at 3 mg/kg is used as a positive control.

Method: The baseline pressure required to induce vocalization or withdrawal of the paw of male Sprague Dawley rats (weighing approximately 180 g, supplied by Iffa Credo, France) is measured (2 hours before treatment), followed by an intra-planar injection of 100 μl of a 20% yeast suspension in water in the hind paw. The rats are treated orally with the test compound (3, 10 or 30 mg/kg), diclofenac (3 mg/kg) or vehicle (saline) p.o. 2 hours later (time point 0 hours), and the pressure test is repeated 1 and 2 hours after dosing. Using the standard apparatus supplied by Ugo Basile, Italy, the pressure required to induce vocalisation or paw withdrawal of the compound-treated rats at these time points is compared to that of vehicle-treated animals.

On the basis of these studies, a compound of formula I surprisingly is appropriate for the treatment of pain. The compounds of the formula I or an N-oxide thereof according to the invention also show therapeutic efficacy especially against other disorders dependent on protein kidnase, especially proliferative diseases.

On the basis of their efficacy as inhibitors of VEGF-receptor tyrosine kinase activity, the compounds of the formula I primarily inhibit the growth of bloodvessels and are thus, for example, effective against a number of diseases associated with deregulated angiogenesis, especially diseases caused by ocular neova scularisation, especially retinopathies, such as diabetic retinopathy or age-related macula degeneration, psoriasis, haemangioblastoma, such as haemangioma, mesangial cell proliferative disorders, such as chronic or acute renal diseases, e.g. diabetic nephropathy, malignant nephrosclerosis, thromrbotic microangiopathy syndromes or transplant rejection, or especially inflammatory renal disease, such as glomerulonephritis, especially mesangioproliferative glomerulonephritis, haemolytic-uraemic syndrome, diabetic nephropathy, hypertensive nephrosclerosis, atherora, arterial restenosis, autoimmune diseases, diabetes, endometriosis, chronic asthma, and especially neoplastic diseases (solid tumors, but also leukemias and other "liquid tumors", especially those expressing c-kit, KDR, flt-1 or Flt-3), such as especially breast cancer, cancer of the colon, lung cancer (especially small-cell lung cancer), cancer of the prostate or Kaposi's sarcoma. A compound of formula I (or an N-oxide thereof) inhibits the growth of tumours and is especially suited to preventing the metastatic spread of tumors and the growth of micrometastases.

A compound of formula I can be administered alone or in combination with one or more other therapeutic agents, possible combination therapy taking the form of fixed ciombinatons or the administration of a corrmpound of the invention and one or more other therapeutic agents being staggered or given independently of one another, or the combined administration of fixed combinations and one or more other therapeutic agents. A compound of formula I can besides or in addition be administered especially for tumor therapy in combination with chemotherapy, radiotherapy, immunotherapy, surgical intervention, or a combination of these. Long-term therapy is equally possible as is adjuvant therapy in the context of other treatment strategies, as described above. Other possible treatments are therapy to maintain the patient's status after tumor regression, or even chemopreveritive therapy, for example in patients at risk.

Therapeutic agents for possible combination are especially one or more cytostatic or cytotoxic compounds, for example a chemotherapeutic agent or several selected from the group comprising an inhibitor of polyamine biosynthesis, an inhibitor of protein kinase, especially of serine/threonine protein kinase, such as protein kinase C, or of tyrosine protein kinase, such as epidermal growth factor receptor tyrosine kinase, a cytokine, a negative growth regulator, such as TGF-β or IFN-β, an aromatase inhibitor, a classical cytostatic, and an inhibitor of the interaction of an SH2 domain with a phosphorylated protein.

A compound according to the invention is not only for the (prophylactic and preferably therapeutic) management of humans, but also for the treatment of other warm-blooded animals, for example of commercially useful animals, for example rodents, such as mice, rabbits or rats, or guinea-pigs. Such a compound may also be used as a reference standard in the test systems described above to permit a comparison with other compounds.

In general, the invention relates also to the use of a compound of formula I or a N-oxide thereof for the inhibition of VEGF-receptor tyrosine activity, either in vitro or in vivo.

A compound of formula I or a N-oxide thereof may also be used for diagnostic purposes, for example with tumors that have been obtained from warm-blooded animal "hosts", especially humans, and implanted into mice to test them for decreases in growth after treatment with such a compound, in order to investigate their sensitivity to the said compound and thus to improve the detection and determination of possible therapeutic methods for neoplastic diseases in the original host.

With the groups of preferred compounds of formula I and N-oxides thereof mentioned hereinafter, definitions of substituents from the general definitions mentioned hereinbefore may reasonably be used, for example, to replace more general definitions with more specific definitions or especially with definitions characterized as being preferred.

In particular, the invention relates to the use of a compound of formula I, wherein n is from 1 up to and including 6;

W is O or S;

$R_1$ and $R_3$ represent independently of each other hydrogen, lower alkyl or lower acyl;

$R_2$ represents a cycloalkyl group, an aryl group, or a mono- or bicyclic heteroaryl group comprising one or more ring nitrogen atoms and 0, 1 or 2 heteroatoms independently from each other selected from the group consisting of oxygen and sulfur, which groups in each case are unsubstftuted or substituted by up to three substituents, selected from amino, mono- or disubstituted amino, halogen, lower alkyl, substituted alkyl, lower alkenyl, lower alkynyl, lower alkanoyl, hydroxy, etherified or esterified hydroxy, nitro, cyano, carboxy, esterified carboxy, alkanoyl, benzoyl, carbamoyl, N-mono- or N,N-disubstituted carbamoyl, amidino, guanidino, ureido, mercapto, sulfo, lower alkylthio, phenyl, phenoxy, phenylthio, phenyl-lower alkylthio, alkylphenylthio, lower alkylsulfinyl, phenylsulfinyl, phenyl-lower alkylsulfinyl, alkylphenylsulfinyl, lower alkanesulfonyl, phenylsulfonyl, phenyl-lower alkylsulfonyl, alkylphenylsulfonyl, halogen-lower alkylmercapto, halogen-lower alkylsulfonyl, dihydroxybora (—B(OH)$_2$), heterocyclyl, and lower alkylene dioxy bound at adjacent C-atoms of the ring;

R and R' are independently of each other hydrogen or lower alkyl;

X represents an aryl group, or a mono- or bicyclic heteroaryl group comprising one or more ring nitrogen atoms and 0, 1 or 2 heteroatoms independently from each other selected from the group consisting of oxygen and sulfur, which groups in each case are unsubstituted or substituted by up to three substituents, selected from amino, mono- or disubstituted amino, halogen, lower alkyl, substituted alkyl, lower alkenyl, lower alkynyl, lower alkanoyl, hydroxy, etherified or esterified hydroxy, nitro, cyano, carboxy, esterified carboxy, alkanoyl, benzoyl, carbamoyl, N-mono- or N,N-disubstituted carbamoyl, amidino, guanidino, ureido, mercapto, sulfo, lower alkylthio, phenyl, phenoxy, phenylthio, phenyl-lower alkylthio, alkylphenylthio, lower alkylsulfinyl, phenylsulfinyl, phenyl-lower alkylsulfinyl, alkylphenylsulfinyl, lower alkanesulfonyl, phenylsulfonyl, phenyl-lower alkylsulfonyl, alkylphenylsulfonyl, halogen-lower alkylmercapto, halogen-lower alkylsulfonyl, dihydroxybora (—B(OH)$_2$), heterocyclyl, and lower alkylene dioxy bound at adjacent C-atoms of the ring;

or a N-oxide or a possible tautomer thereof;

or of a pharmaceutically acceptable salt of such a compound for the preparation of a pharmaceutical composition for the treatment of a disease which responds to an inhibition of the VEGF receptor tyrosine kinase activity.

More preferably, the invention relates to the use of a compound of formula I, wherein n is from 1 up to and including 3;

W is O or S;

$R_1$ and $R_3$ represent independently of each other hydrogen, lower alkyl or lower acyl;

$R_2$ represents cyclohexyl, phenyl, indazolyl, thiazolyl, benzo[d]thiazolyl, benzo[d]pyrazolyl or isoquinolinyl, which in each case is unsubstituted or mono- or disubstituted by lower alkyl, lower alkenyl or lower alkynyl; and wherein each radical $R_2$ can be unsubstituted or mono- or polysubstituted with halogen;

R and R' are independently from each other hydrogen or lower alkyl

X represents phenyl, pyridyl, pyrimidyl or quinolyl, which in each case is unsubstituted or mono- or polysubstituted by oxo, hydroxy, lower alkyl or lower alkoxy;

or a N-oxide or a possible tautomer thereof;

or of a pharmaceutically acceptable salt of such a compound for the preparation of a pharmaceutical composition for the treatment of a disease which responds to an inhibition of the VEGF receptor tyrosine kinase activity.

One preferred embodiment of the invention relates to a compound of the formula I, wherein n is 1 or 2;

W is O;

$R_1$ and $R_3$ represent hydrogen;

$R_2$ represents cyclohexyl, phenyl, indazolyl, thiazolyl or isoquinolinyl, which in each case is unsubstitutedor mono- or disubsfituted by lower alkyl or lower alkynyl; and wherein each radical $R_2$ can be unsubstituted or mono- or polysubstituted with halogen;

R and R' are independently from each other hydrogen or lower alkyl;

X represents phenyl, pyridyl, pyrimidyl or quinolyl, which in each case is unsubstituted or mono- or polysubstituted by oxo, hydroxy, lower alkyl or lower alkoxy;

or a N-oxide or a possible tautomer thereof;

or of a pharmaceutically acceptable salt of such a compound is used for the preparation of a pharmaceutical composition for the treatment of a disease which responds to an inhibition of the VEGF receptor tyrosine kinase activity.

Especially, the invention relates to the use of a compound of formula I or of a N-oxide or a possible tautomer thereof or of a pharmaceutically acceptable salt of such a compound for the preparation of a pharmaceutical composition for the treatment of a disease which responds to an inhibition of the VEGF-receptor tyrosine kinase activity, wherein the disease is a neoplastic disease.

In another preferred embodiment of the invention, the invention relates to the use of a compound of the formula I or of a N-oxide or a possible tautomer thereof; or of a pharmaceutically acceptable salt of such a compound for the preparation of a pharmaceutical composition for the treatment of a disease which responds to an inhibition of the VEGF-receptor tyrosine kinase activity, wherein the disease is retinopathy or age-related macular degeneration.

Furthermore, the invention provides a method for the treatment of a disease which responds to an inhibition of the VEGF-receptor tyrosine kinase activity, which comprises administering a compound of formula I or a Noxide or a pharmaceutically acceptable salt thereof, wherein the radicals and symbols have the meanings as defined above, in a quantity effective against said disease, to a warm-blooded animal requiring such treatment.

Moreover, the invention relates to compounds of the formula I, wherein n is from 1 up to and including 6;

W is O or S;

$R_1$ and $R_3$ represent independently of each other hydrogen, lower alkyl or lower acyl;

$R_2$ represents an cycloalkyl group, an aryl group, or a mono- or bicyclic heteroaryl group comprising one or more ring nitrogen atoms and 0, 1 or 2 heteroatoms independently from each other selected from the group consisting of oxygen and sulfur, which groups in each case are unsubstituted or mono- or polysubstituted;

R and R' are independently of each other hydrogen or lower alkyl;

X represents an aryl group, or a mono- or bicyclic heteroaryl group comprising one or more ring nitrogen atoms and 0, 1 or 2 heteroatoms independently from each other selected from the group consisting of oxygen and sulfur, which groups in each case are unsubstituted or mono- or polysubstituted;

and N-oxides and possible tautomers thereof;

and to pharmaceutically acceptable salts of such compounds, with the exception of the compounds of formula I wherein n is 1, W is O, $R_1$, $R_3$, R, R' are hydrogen, X is phenyl and $R_2$ is 3-trifluoromethylphenyl or 2-methoxyphenyl.

More preferably, the Invention relates to compounds of the formula I, wherein n is from 1 up to and including 6;

W is O or S;

$R_1$ and $R_3$ represent independently of each other hydrogen, lower alkyl or lower acyl;

R₂ represents a cycloalkyl group, an aryl group, or a mono- or bicyclic heteroaryl group comprising one or more ring nitrogen atoms and 0, 1 or 2 heteroatoms independently from each other selected from the group consisting of oxygen and sulfur, which groups in each case are unsubstituted or.substituted by up to three substituents, selected from amino, mono- or disubstituted amino, halogen, lower alkyl, substituted alkyl, lower alkenyl, lower alkynyl, lower alkanoyl, hydroxy, etherfied or esterified hydroxy, nitro, cyano, carboxy, esterified carboxy, alkanoyl, benzoyl, carbamoyl, N-mono- or N,N-disubstituted carbamoyl, amidino, guanidino, ureido, mercapto, sulfo, lower alkylthio, phenyl, phenoxy, phenylthio, phenyl-lower alkylthio, alkylphenylthio, lower alkylsulfinyl, phenylsulfinyl, phenyl-lower alkylsulfinyl, alkylphenylsulfinyl, lower alkanesulfonyl, phenylsulfonyl, phenyl-lower alkylsulfonyl, alkylphenylsulfonyl, halogen-lower alkylmercapto, halogen-lower alkylsulfonyl, dihydroxybora (—B(OH)₂), heterocyclyl, and lower alkylene dioxy bound at adjacent C-atoms of the ring;

R and R' are independently of each other hydrogen or lower alkyl;

X represents an aryl group, or a mono- or bicyclic heteroaryl group comprising one or more ring nitrogen atoms and 0, 1 or 2 heteroatoms independently from each other selected from the group consisting of oxygen and sulfur, which groups in each case are unsubstituted or substituted by up to three substituents, selected from amino, mono- or disubstituted amino, halogen, lower alkyl, substituted alkyl; lower alkenyl, lower alkynyl, lower alkanoyl, hydroxy, etherified or esterified hydroxy, nitro, cyano, carboxy, esterified carboxy, alkanoyl, benzoyl, carbamoyl, N-mono- or N,N-disubstituted carbamoyl, amidino, guanidino, ureido, mercapto, sulfo, lower alkylthio, phenyl, phenoxy, phenylthio, phenyl-lower alkylthio, alkylphenylthio, lower alkylsulfinyl, phenylsulfinyl, phenyl-lower alkylsulfinyl, alkylphenylsulfinyl, lower alkanesulfonyl, phenylsulfonyl, phenyl-lower alkylsulfonyl, alkylphenylsulfonyl, halogen-lower alkylmercapto, halogen-lower alkylsulfonyl, dihydroxybora (—B(OH)₂), heterocyclyl, and lower alkylene dioxy boundat adjacent C-atoms of the ring;

or N-oxides or possible tautomers thereof;
or pharmaceutically acceptable salts of such compounds; with the exception of the compounds of formula I wherein n is 1, W is O, R₁, R₃, R, R' are hydrogen, X is phenyl and R₂ is 3-trifluoromethylphenyl or 2-methoxyphenyl.

Preferred are compounds of the formula I, wherein
n is from 1 up to and including 3;
W is O or S;
R₁ and R₃ represent iridependently of each other hydrogen, lower alkyl or lower acyl;
R₂ represents cyclohexyl, phenyl, indazolyl, thiazolyl, benzo[d]thiazolyl, benzo[d]pyrazolyl or isoquinolinyl, which in each case is unsubstituted or mono- or disubstituted by lower alkyl, lower alkenyl or lower alkynyl; and
wherein each radical R₂ can be unsubstituted or mono- or polysubstituted with halogen;
R and R' are independently from each other hydrogen or lower alkyl;
X represents phenyl, pyridyl, pyrimidyl or quinolyl, which in each case is unsubstituted or mono- or polysubstituted by oxo, hydroxy, lower alkyl or lower alkoxy;

or N-oxides or possible tautomers thereof;
or pharmaceutically acceptable salts of such compounds; with the exception of the compounds of formula I wherein n is 1, W is O, R₁, R₃, R, R' are hydrogen, X is phenyl and R₂ is 3-trifluoromethylphenyl or 2-methoxyphenyl.

Especially preferred is a compound of formula I, wherein
n is 1 or 2;
W is O;
R₁ and R₃ represent hydrogen;
R₂ represents cyclohexyl, phenyl, indazolyl, thiazolyl or isoquinolinyl, which in each case is unsubstituted or mono or disubstituted by lower alkyl or lower alkynyl; and
wherein each radical R₂ can be unsubstituted or mono- or polysubstituted with halogen;
R and R' are independently from each other hydrogen or lower alkyl;
X represents phenyl, pyridyl, pyrimidyl or quinolyl, which in each case is unsubstituted or mono- or polysubstituted by oxo, hydroxy, lower alkyl or lower alkoxy;

or a N-oxide or a possible tautomer thereof;
or a pharmaceutically acceptable salt of such a compound; with the exception of the compounds of formula I wherein n is 1, R, R' are hydrogen, X is phenyl and R₂ is 3-trifluoromethylphenyl or 2-methoxyphenyl.

In the definition of R₂ above the wording "wherein each radical R₂ can be unsubstituted or mono- or polysubstituted with halogen" denotes a radical R₂ wherein also the substituents lower alkyl, lower alkenyl or lower alkynyl on the groups mentioned (cyclohexyl, phenyl, indazolyl, etc) are themselves optionally substituted by halogen. Therefore, the definiton comprises inter alia radicals R₂ like trifluoromethylphenyl or bis(trifluoromethyl)-phenyl.

High preference is given to a compound selected from the group of compounds consisting of 2-[2-(4-Pyridyl)ethyl]amino-N-[3-(trifluoromethyl)phenyl]3-pyridinecarboxamide, 2-[(4-Pyridyl)methyl]amino-N-[3-(trifluoromethyl)phenyl]-3-pyridinecarboxamide, 2-[(2-Methyl-4-pyridyl)methyl]amino-N-[3-trifluoromethyl)phenyl]-3-pyridinecarboxamide, 2-[(6-Methoxy-3-pyridyl)methyl]amino-N-[3-(trifluoromethyl)phenyl]-3-pyridinecarboxamide, 2-[(4-Pyridyl)methyl]amino-N-[3,4-bis(trifluoromethyl)-phenyl]-3-pyridinecarboxamide, 2-[(4-Pyridyl)methyl]amino-N-[5-fluoro-3-tritluoromethyl-phenyl]-3-pyridinecarboxamide, 2-[(4-Pyridyl)methyl]amino-N-(trans-4-tert-butyl-cyclohexane)-3-pyridinecarboxamide, 2-[(4-Pyridyl)methyl]amino-N-(4-n-propyl-phenyl)-3-pyridinecarboxamide, 2-[(4-Pyridyl)methyl]amino-N-(4n-butyl-phenyl)-3-pyridinecarboxamide, 2-[(4-Pyridyl)methyl]amino-N-(4-n-pentyl-phenyl)-3-pyridinecarboxamide, 2-[(4-Pyridyl)methyl]amino-N-[4-(1-propynyl)-phenyl]-3-pyridinecarboxamide, 2-[(4-Pyridyl)methyl]amino-N-(5-indazolyl)-3pyridinecarboxamide, 2-[(4-Pyridyl)methyl]amino-N-(3-isoquinolinyl)-3-pyridinecarboxamide, 2-[(Pyridin-6(1H)-on-3-yl)methyl]amino-N-[3-(trifluoromethyl)phenyl]-3-pyridinecarboxamide, and the pharmaceutically acceptable salt thereof.

Furthermore, high preference is given to a compound selected from the group of compounds consisting of 2(Phenylmethylamnino-N-[3-(trifluoromethyl)phenyl]-3-pyridine-carboxamide, hydrochloride, 2-[(4-Pyridyl)methylamino]-N-[2-fluoro-3-(trifluoromethyl)phenyl]-3-pyridinecarboxamide, 2-[(4-Pyridyl)methylamino]-N-[4-bromo-3-(trifluoromethyl)phenyl]-3-pyridinecarboxamide, 2-[(4-Pyridyl)methylamino]-N-[2-methyl-3-(trifluoromethyl)phenyl]-3-pyridinecarboxamide, 2-[(4-Pyridyl)methylamino]-N-[2-methyl-5-(trifluoromethyl)phenyl]-3-pyridinecarboxamide, 2-[(4-Pyridyl)methylamino]-N-(cis-4-tert-butyl-cyclohexyl)-3-pyridinecarboxamide, 2-[(6-Methoxypyrid-3-yl)methylamino]-N-[4-bromo-3-trifluoromethyl)phenyl]-3-pyridinecarboxamide, 2-[(6Methoxypyrid-3-yl)methylamino]-N-[2-fluoro-3-(trifluoromethyl)phenyl]-3-pyridinecarboxarnide, 2-[(6-Methoxypyrid-3-yl)methylamino]-N-[2-methyl-3-(trifluoromethyl)phenyl]-3-pyridinecarboxamide, 2-[(1-Oxido-4-pyridyl)methylamino]-N-[3-(trifluoromethyl)phenyl]-3-pyridinecarboxamide, 2-[(3-(N-methyl-carboxamido)phenyl[methylamino]-N-[3-(trifluoromethyl)phenyl]-3-pyridinecarboxamide, 2-[(1-Methyl-pyridin-2(1H)-on-5-yl)methylamino]-M-[3-(trifluoromethyl)phenyl-3-pyridinecarboxamide, 2-[(6-Methoxypyrid-3-yl)methylamino]-N-4-propynyl-3-(trifluoromethyl)phenyl]-3-pyridinecarboxamide, 2-[(4-Pyridyl)methylamino]-N-[4propynyl-3-(trifluoromethyl)phenyl ]-3-pyridinecarboxamide, 2-[(Pyridin-2(1H)-on-5-yl)methyl]amino-N-[4propynyl-3-(trifluoromethyl)phenyl]-3-pyridinecarboxamide, 2-[(Pyridin-2(1H)-on-5-yl)methyl]amino-N-[3-(trifluoromethyl, phenyl]-3-pyridinecarboxamide, 2-[(3-Hydroxyphenyl)methyl]amino-N-[3-(trifluoromethyl)phenyl]-3-pyridinecarboxamide, 2-[(Pyridin-2(1H)-on-5-yl)methyl]amino-N-[4-bromo-3-(trifluoromethyl)phenyl]-3-pyridinecarboxamide, 2-[(Pyridin-2(1H)-on-5-yl)methyl]amino-N-[2-fluoro-3-(trifluoromethyl)phenyl]-3-pyridinecarboxamide, 2-[(Pyridin-2(1H)-on-5-yl)methyl]amino-N-[2-methyl-(trifluoromethyl)phenyl]-3-pyridinecarboxamide, 2-[(Pyridin-2(1H)-on-5-yl)methyl]amino-N-[4-propyl-(trifluoromethyl)phenyl]4-pyridinecarboxamide, 2-[(6-Methoxypyrid-3-yl)methylamino]-N-[4-propyl-3-trifluoromethyl)phenyl]-3-pyridinecarboxamide, 2-[(4-Pyridyl)methyl]amino-N-4-(n-propyl)-3-(trifluoromethyl)phenyl]-3-pyridinecarboxamide, 2-[(4-Pyridyl)methyl]amino-N-(5-thiazolyl)-3-pyridinecarboxamide, 2-[(4-Hydroxyphenyl)methyl]amino-N-[3-(trifluoromethyl)phenyl]-3-pyridine-carboxamide, 2-[(4-Pyridyl)methyl]amino-N-benzo[d]pyrazol-5-yl)-3-pyridinecarboxamide, 2-[(6-Methoxy-3-pyridyl)methyl]amino-N-(3-isoquinolinyl)-3-pyridinecarboxamide, 2-[(6-Methoxy-3-pyridyl)methyl[amino-N-(benzo[d]pyrazol-5-yl)-3-pyridinecarboxamide, 2-[(Pyridin-2(1H)-on-5-yl)methyl]amino-N-(3-isoquinolinyl)-3-pyridinecarboxamide, 2-[(Pyridin-2(1H)-on-5-yl)methyl]amino-N-(benzo[d]pyrazol-5-yl)-3-pyridinecarboxamide, 2-[(Pyridin-2(1H)-on-5-yl)methyl]amino-N-(cis-4-tert-butyl-cyclohexyl)3-pyridinecarboxamide, 2-[(Pyridin-2(1H)-on-5-yl)methyl]amino-N-(trans-4-tert-butyl-cyclohexyl)-3-pyridinecarboxamide, 2-[(1-Oxido-4-pyridyl)methylamino]-N-[4-propyl-3-(trifluoromethyl)phenyl]-3-pyridinecarboxamide, 2-[(Pyridin-2(1H)-on-5-yl)methyl]amino-N-[4-ethyl-3-(trifluoromethyl)phenyl]-3-pyridinecarboxamide, 2-[(Pyridin-2(1H)-on-5-yl)methyl]amino-N-[3,4-bis(trifluoromethyl)phenyl]-3-pyridinecarboxamide, 2-[(1-Methyl-pyridin-2(1H)-on-5-yl)methylamino]-N-[3,4-bis(trifluoromethyl)phenyl]-3-pyridinecarboxamide, and the pharmaceutically acceptable salts thereof.

A compound of the invention may be prepared by processes that, though not applied hitherto for the new compounds of the present invention, are known per se, especially a process characterized in that for the synthesis of a compound of the formula I wherein the symbols $R_1$, $R_2$, $R_3$, R, R', X, W and n are as defined for a compound of the formula I, an pyridine derivative of the formula II

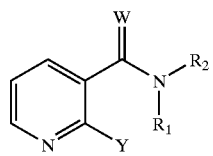

(II)

wherein W, $R_1$ and $R_2$ are as defined for a compound of the formula I and Y is a leaving group, such as a halogen, preferably chloro, is reacted with an amine of the formula III

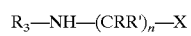

(III)

$R_3$—NH—(CRR')$_n$—X wherein n, R, R', $R_3$ and X are as defined for a compound of the formula I, optionally in the presence of a base and a suitable catalyst, such as a copper(I) compound optionally in the presence of an inert solvent;

where the above starting compounds II and III may also be present with functional groups in protected form if necessary and/or in the form of salts, provided a salt-forming group is present and the reaction in salt form is possible;

any protecting groups in a protected derivative of a compound of the formula I are removed;

and, if so desired, an obtainable compound of formula I is converted into another compound of formula I or a N-oxide thereof, a free compound of formula I is converted into a salt, an obtainable salt of a compound of formula I is converted into the free compound or another salt, and/or a mixture of isomeric compounds of formula I is separated into the individual isomers.

Alternatively, a cormpound of the invention wherein R' attached to the carbon atom bound to the nitrogen atom in the bridging group is hydrogen may be prepared by a process in which an aminopyridine of formula IV

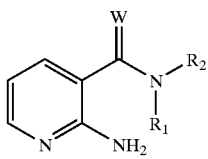

(IV)

wherein $R_1$ and $R_2$ are as defined for a compound of the formula I is reacted with a carbonyl compound of the formula V

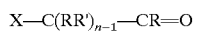

$$X\text{—}C(RR')_{n-1}\text{—}CR\text{=}O \qquad (V)$$

wherein X, n, R and R' are as defined for a compound of the formula I in the presence of a reducing agent. The carbonyl compound of the formula V may also be present in the form of reactive derivative; however, the free aldehyde or ketone is preferred. Reactive derivatives of the compounds of formula V are, for example, corresponding bisulfite adducts or especially semiacetals, acetals, semiketals or ketals of compounds of formula V with alcohols, for example lower alkanols; or thioacetals or thioketals of compounds of formula V with mercaptans, for example lower alkanesulfides.

The reductive alkylation is preferably carried out with hydrogenation in the presence of a catalyst, especially a noble metal catalyst, such as platinum or especially palladium, which is preferably bonded to a carrier material, such as carbon, or a heavy metal catalyst, such as Raney nickel, at normal pressure or at prossures of from 0.1 to 10 MegaPascal (MPa), or with reduction by means of complex hydrides, such as borohydrides, especially alkali metal cyanoborohydrides, for example sodium cyanoborohydride, in the presence of a suitable acid, preferably relatively weak acids, such as lower alkanecarboxylic acids, especially acetic acid, or a sulfonic acid, such as p-toluenesulfonic acid; in customary solvents, for example alcohols, such as methanol or ethanol, or ethers, for example cyclic ethers, such as tetrahydrofuran, in the presence or absence of water.

Detailed Description of the Process

In the more detailed description of the process below $R_1$, $R_2$, $R_3$, R, R', X, W and n are as defined for compounds of formula I, unless otherwise indicated.

The reaction of compounds of formula II and III is preferably carried out in a polar solvent, for example in alcohols, e.g. ethanol, isopropanol, butanol, 3-ethyl-3-pentanol, in dimethylacetamide-, dimethylformamide or N-methylpyrrolidone and preferably under an inert atmosphere, for example under a nitrogen or an argon atmosphere. The base that is used in the reaction can be selected from customary bases, such as potassium carbonate, caesium carbonate or an organic base such as a tretiary amine, such as ethyldiisopropylamine, or an aromatic amine such as pyridine, or in the presence of an excess of the reagent of formula III. Good results were obtained with potassium carbonate. The reaction is catalysed by copper ion catalysts or nickel salts. Preferably, copper(I)oxide or copper (I)-iodide is used as the catalyst. The compounds are preferably reacted between 0.5 and 24 hours, e.g. 120 minutes, between room temperature and the reflux temperature of the solvent. If dimethylformamide is chosen as the solvent for the reaction, the temperature is e.g. preferably in the range of 80° C. up to the reflux temperature of the solvent.

Protecting Groups

If one or more other functional groups, for example carboxy, hydroxy, amino, or mercapto, are or need to be protected in a compound of formula II, III and/or IV, because they should not take part in the reaction, these are such groups as are usually used in the synthesis of peptide compounds, and also of cephalosporins and penicillins, as well as nucleic acid derivatives and sugars.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products.The specialist knows, or can easily establish, which protecting groups are suitable with the reactions mentioned hereinabove and hereinafter.

The protection of such functional groups by such protecting groups, the protecting groups themselves, and their removal reactions are described for example in standard reference works, such as J. F. W. McOmie, "Protective Groups in Organic Chemistry", Plenum Press, London and New York 1973, in T. W. Greene, "Protective Groups in Organic Synthesis", Wiley, New York 1981, in "The Peptides"; Volume 3 (editors: E. Gross and J. Meienhofer), Academic Press, London and New York 1981, in "Methoden der organischen Chemie" (*Methods of organic chemistry*), Houben Weyl, 4th edition, Volume 1511, Georg Thieme Verlag, Stuttgart 1974, in H. -D. Jakubke and H. Jescheit, "Aminosäuren, Peptide, Proteine" (*Amino acids, peptides, proteins*), Verlag Chemie, Weinheim, Deerfield Beach, and Basel 1982, and in Jochen Lehmann, "Chemie der Kohlenhydrate: Monosaccharide und Derivate" (*Chemistry of carbohydrates: monosaccharides and derivatives*), Georg Thieme Verlag, Stuttgart 1974.

In one embodiment of the invention a compound of formula I comprising a 2-methoxypyridyl radical is transferred into a compound of formula I comprising a 2-hydroxypyridyl radical by treatment with trimethylsilyl iodide for about 20 to 35 hours at a temperature between 45° C. and 70° C. in a suitable solvent, e.g. a halogenated alkane, like chloroform, optionally followed by treatment with methanol.

Additional Process Steps

In the additional process steps, carried out as desired, functional groups of the starting compounds which should not take part in the reaction may be present in unprotected form or may be protected for example by one or more of the protecting groups mentioned hereinabove under "protecting groups". The protecting groups are then wholly or partly removed according to one of the methods described there.

Salts of a compound of formula I with a salt-forming group may be prepared in a manner known per se. Acid addition salts of compounds of formula I may thus be obtained by treatment with an acid or with a suitable anion exchange reagent. A salt with two acid molecules (for example a dihalogenide of a compound of formula 1) may also be converted into a salt with one acid molecule per compound (for example a monohalogenide); this may be done by heating to a melt, or for example by heating as a solid under a high vacuum at elevated temperature, for example from 130 to 170° C., one molecule of the acid being expelled per molecule of a compound of formula I.

Salts can usually be converted to free compounds, e.g. by treating with suitable basic agents, for example with alkali metal carbonates, alkali metal hydrogencarbonates, or alkali metal hydroxides, typically potassium carbonate or sodium hydroxide.

Stereoisomerc mixtures, e.g. mixtures of diastereomers, can be separated into their corresponding isomers in a manner known per se by means of suitable separation methods. Diastereomeric mixtures for example may be separated into their individual diastereomers by means of fractionated crystallization, chromatography, solvent distribution, and similar procedures. This separation may take place either at the level of a starting compound or in a compound of formula I itself. Enantiomers may be separated through the formation of diastereomeric salts, for example by salt formation with an enantiomerpure chiral acid, or by means of chromatography, for example by HPLC, using chromatographic substrates with chiral ligands.

A compound of formula I, wherein W is O, can be converted into the respective compound wherein W is S, for example, by using an appropriate sulfur compound, e.g. using reaction with Lawesson's reagent (2,4bis-(4-methoxyphenyl)2,4-dithloxo-1,2,3,4dithiaphosphetan) in a halogenated carbon hydrate, such as dichloromethane, or an aprotic solvent, such as toluene or xylene, at temperatures from about 30° C. to reflux.

A compound of the formula I wherein $R_1$ is hydrogen can be converted to the respective compound wherein $R_1$ is lower alkyl by reaction e.g. with a diazo lower alkyl compound, especially diazomethane, in an inert solvent, preferably in the presence of a noble metal catalyst, especially in dispersed form, e.g. copper, or a noble metal salt, e.g. copper(I)-chloride or copper(II)-sulfate. Also reaction with lower alkylhalogenides is possible, or with other leaving group carrying lower alkanes, e.g. lower alkyl alcohols esterified by a strong organic sulfonic acid, such as a lower alkane sulfonic acid (optionally substituted by halogen, such as fluoro), an aromatic sulfonic acid, for example unsubstituted or substituted benzene-sulfonic acid, the substituents preferably being selected from lower alkyl, such as methyl, halogen, such as bromo, and/or nitro, e.g. esterified by methane sulfonic acid, trimethane sulfonic acid or p-toluol sulfonic acid. The alkylation takes place especially in aqueous solution and/or in the presence of polar solvents, typically alcohols, for example methanol, ethanol, isopropanol, or ethylene glycol, ethers, typically dioxane, amides, typically dimethylformamide, or phenols, typically phenol, and also under non-aqueous conditions, in non-polar solvents, typically benzene and toluene, or in benzene/water emulsions, where applicable in the presence of acidic or basic catalysts, for example leaches, typically sodium hydroxide solution, or in the presence of solid-phase catalysts, typically aluminium oxide, that have been doped with hydrazine, in ethers, for example diethylether, generally at temperatures from about 0° C. to the boiling temperature of the corresponding reaction mixture, preferably between 20° C. and reflux temperature, if necessary under increased pressure, e.g. in a sealed tube, a temperature in excess of boiling point also being possible, and/or under inert gas, typically nitrogen or argon.

It should be emphasized that reactions analogous to the conversions mentioned in this chapter may also take place at the level of appropriate intermediates.

General Process Conditions

All process steps described here can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralising agents, for example ion exchangers, typically cation exchangers, for example in the $H^+$ form, depending on the type of reaction and/or reactants at reduced, normal, or elevated temperature, for example in the range from –100° C. to about 190° C., preferably from about –80° C. to about 150° C., for example at –80 to –60° C., at room temperature, at –20 to 40° C. or at the boiling point of the solvent used, under atmospheric pressure or in a dosed vessel, where approprate under pressure, and/or in an inert atmosphere, for example under argon or nitrogen.

Salts may be present in all starting compounds and transients, if these contain salt-forming groups. Salts may also be present during the reaction of such compounds, provided the reaction is not thereby disturbed.

At all reaction stages, isomeric mixtures that occur can be separated into their individual isomers, e.g. diastereomers or enantiomers, or into any mixtures of isomers, e.g. racemates or diastereomeric nixtures, typically as described under "Additional process steps".

In certain cases, typically in hydrogenation processes, it is possible to achieve stereoselective reactions, allowing for example easier recovery of individual isomers.

The solvents from which those can be selected which are suitable for the reaction in question include for example water, esters, typically lower alkyl-lower alkanoates, e.g diethyl acetate, ethers, typically aliphatic ethers, e.g. diethylether, or cyclic ethers, e.g. tetrahydrofuran, liquid-aromatic hydrocarbons, typically benzene or toluene, alcohols, typically methanol, ethanol or 1- or 2-propanol, nitrites, typically acetonitrile, halogenated hydrocarbons, typically dichloromethane, acid amides, typically dimethylformamide, bases, typically heterocyclic nitrogen bases, e.g. pyridine, carboxylic acids, typically lower alkanecarboxylic acids, e.g. acetic acid, carboxylic acid anhydrides, typically lower alkane acid anhydrides, e.g. acetic anhydride, cyclic, linear, or branched hydrocarbons, typically cyclohexane, hexane, or isopentane, or mixtures of these solvents, e.g. aqueous solutions, unless otherwise stated in the description of the process. Such solvent mixtures may also be used in processing, for example through chromatography or distribution.

The invention relates also to those forms of the process in which one starts from a compound obtainable at any stage as a transient and carries out the missing steps, or breaks off the process at any stage, or forms a startng material under the reaction conditions, or uses said starting material in the form of a reactive derivative or salt, or produces a compound obtainable by means of the process according to the invention and processes the said compound in situ. In the preferred embodiment, one starts from those starting materials which lead to the compounds described hereinabove as preferred, particularly as especially preferred, primarily preferred, and/or preferred above all.

In the preferred embodiment, a compound of formula I is prepared according to or in analogy to the processes and process steps defined in the Examples.

The compounds of formula I, including their salts, are also obtainable in the form of hydrates, or their crystals can include for example the solvent used for crystallization (present as solvates).

Pharmaceutical Preparations, Methods, and Uses

The present invention relates furthermore to a method for the treatment of a neoplastic disease which responds to an inhibition of the VEGF-receptor tyrosine kinase activity, which comprises administering a compound of formula I or a N-oxide or a pharmaceutically acceptable salt thereof, wherein the radicals and symbols have the meanings as defined above for formula I, in a quantity effective against said disease, to a warm-blooded animal requiring such treatment.

In another embodiment the invention relates to a method for the treatment of retinopathy or age-related macular degeneration, which comprises administering a compound of formula I or a N-oxide or a pharmaceutically acceptable salt thereof, wherein the radicals and symbols have the meanings as defined above for formula I, in a quantity effective against said diseases, to a warm-blooded animal requiring such treatment.

The present invention relates also to pharmaceutical compositions that comprise a compound of formula I or a N-oxide thereof as active ingredient and that can be used especially in the treatment of the diseases mentioned at the beginning. Compositions for enteral administration, such as nasal, buccal, rectal or, especially, oral administration, and for parenteral administration, such as intravenous, intramuscular or subcutaneous administration, to warm-blooded animals, especially humans, are especially preferred. The compositions comprise the active ingredient alone or, preferably, together with a pharmaceutically acceptable carrier. The dosage of the active ingredient depends upon the disease to be treated and upon the species, its age, weight and individual condition, the individual pharmacokinetic data, and the mode of administration.

The present invention relates especially to pharmaceutical compositions that comprise a compound of formula I, a tautomer, a N-oxide or a pharnaceutically acceptable salt, or a hydrate or solvate thereof, and at least one pharmaceutically acceptable carrier.

The invention relates also to pharmaceutical compositions for use in a method for the prophylactic or especially therapeutic management of the human or animal body, to a process for the preparation thereof (especially in the form of compositions for the treatment of tumors) and to a method of treating tumor diseases, especially those mentioned hereinabove.

The invention relates also to processes and to the use of compounds of formula I or N-oxides thereof for the preparation of pharmaceutical preparations which comprise compounds of formula I or N-oxides thereof as active component (active ingredient).

In the preferred embodiment, a pharmaceutical preparation is suitable for administration to a warm-blooded animal, especially humans or commercially useful mammals suffering from a disease responsive to an inhibition of angiogenesis or of VEGF-receptor tyrosine kinase, for example psoriasis or especially a neoplastic disease, and comprises an effective quantity of a compound of formula I or N-oxides thereof for the inhibition of angiogenesis or of VEGF-receptor tyrosine kinase, or a pharmaceutically acceptable salt thereof, if salt-forming groups are present, together with at least one pharmaceutically acceptable carrier.

A pharmaceutical composition for the prophylactic or especially therapeutic management of neoplastic and other proliferative diseases of a warm-blooded animal, especially a human or a commercially useful mammal requiring such treatment, especially suffering from such a disease, comprising as active ingredient in a quantity that is prophylactically or especially therapeutically active against the said diseases a novel compound of formula I or N-oxides thereof, is likewise preferred.

The pharmaceutical compositions comprise from approximately 1% to approximately 95% active ingredient, single-dose administration forms comprising in the preferred embodiment from approximately 20% to approximately 90% active ingredient and forms that are not of single-dose type comprising in the preferred embodiment from approximately 5% to approximately 20% active ingredient. Unit dose forms are, for example, coated and uncoated tablets, ampoules, vials, suppositories, or capsules. Further dosage forms are, for example, ointments, creams, pastes, foams, tinctures, lip-sticks, drops, sprays, dispersions, etc. Examples are capsules containing from about 0.05 g to about 1.0 g active ingredient.

The pharmaceutical compositions of the present invention are prepared in a manner known per se, for example by means of conventional mixing, granulating, coating, dissolving or lyophilizing processes.

Preference is given to the use of solutions of the active ingredient, and also suspensions or dispersions, especially isotonic aqueous solutions, dispersions or suspensions which, for example in the case of lyophilized compositions comprising the active ingredient alone or together with a carrier, for example mannitol, can be made up before use. The pharmaceutical compositions may be sterilized and/or rnay comprise excipients, for example preservatives, stabilizers, wetting agents and/or emulsifiers, solubilizers, salts for regulating osmotic pressure and/or buffers and are prepared in a manner known per se, for example by means of conventional dissolving and lyophilizing processes. The said solutions or suspensions may comprise viscosity-increasing agents, typically sodium carboxymethylcellulose, carboxymethylcellulose, dextran, polyvinylpyrrolidone, or gelatins, or also solubilizers, e.g. Tween 80® [polyoxyethylene(20)sorbitan mono-oleate; trademark of ICI Americas, Inc, USA].

Suspensions in oil comprise as the oil component the vegetable, synthetic, or semi-synthetic oils customary for injection purposes. In respect of such, special mention may be made of liquid fatty acid esters that contain as the acid component a long-chained fatty acid having from 8 to 22, especially from 12 to 22, carbon atoms, for example lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brassidic acid or linoleic acid, if desired with the addition of antioxidants, for example vitamin E, β-carotene or 3,5-di-tert-butyl-4-hydroxytoluene. The alcohol component of these fatty acid esters has a maximum of 6 carbon atoms and is a monovalent or polyvalent, for example a mono-, di- or trivalent, alcohol, for example methanol, ethanol, propanol, butanol or pentanol or the isomers thereof, but especially glycol and glycerol. As fatty acid esters, therefore, the following are mentioned: ethyl oleate, isopropyl myristate, isopropyl palmitate, "Labrafil M 2375" (polyoxyethylene glycerol trioleate from Gattefossé, Paris), "Labrafil M 1944 CS" (unsaturated polyglycolized glycerides prepared by alcoholysis of apricot kernel oil and consisting of glycerides and polyethylene glycol ester; Gattefossé, France), "Labrasol" (saturated polyglycolized glycerides prepared by alcoholysis of TCM and consisting of glycerides and polyethylene glycol ester; Gattefossé, France), and/or "Miglyol 8120" (triglyceride of saturated fatty acids of chain length $C_8$ to $C_{12}$ from Hüls AG, Germany), but especially vegetable oils such as cottonseed oil, almond oil, olive oil, castor oil, sesame oil, soybean oil and more especially groundnut oil.

The manufacture of injectable preparations is usually carried out under sterile conditions, as is the filling, for example, into ampoules or vials, and the sealing of the containers.

Pharmaceutical compositions for oral administration can be obtained, for example, by combining the active ingredient with one or more solid carriers, if desired granulating a resulting mixture, and processing the mixture or granules, if desired or necessary, by the inclusion of additional excipients, to form tablets or tablet cores.

Suitable carriers are especially fillers, such as sugars, for example lactose, saccharose, mannitol or sorbitol, cellulose preparations, and/or calcium phosphates, for example tricalcium phosphate or calcium hydrogen phosphate, and also binders, such as starches, for example corn, wheat, rice or potato starch, methylcellulose, hydroxypropyl methylcellulose, sodium carboxymethylcellulose, and/or polyvinylpyrrolidone, and/or, if desired, disintegrators, such as the above-mentioned starches, also carboxymethyl starch, crosslinked polyvinylpyrrolidone, alginic acid or a salt thereof, such as sodium alginate. Additional excipients are especially flow conditioners and lubricants, for example silicic acid, talc, stearic acid or salts thereof, such as magnesium or calcium stearate, and/or polyethylene glycol, or derivatives thereof.

Tablet cores can be provided with suitable, optionally enteric, coatings through the use of, inter alia, concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes or pigments may be added to the tablets or tablet coatings, for example for identification purposes or to indicate different doses of active ingredient.

Pharmaceutical compositions for oral administration also include hard capsules consisting of gelatin, and also soft, sealed capsules consisting of gelatin and a plasticizer, such as glycerol or sorbitol. The hard capsules may contain the active ingredient in the form of granules, for example in admixture with fillers, such as corn starch, binders, and/or glidants, such as talc or magnesium stearate, and optionally stabilizers. In soft capsules, the active ingredient is preferably dissolved or suspended in suitable liquid excipients, such as fatty oils, paraffin oil or liquid polyethylene glycols or fatty acid esters of ethylene or propylene glycol, to which stabilizers and detergents, for example of the polyoxyethylene sorbitan fatty acid ester type, may also be added.

Pharmaceutical compositions suitable for rectal administration are, for example, suppositories that consist of a combination of the active ingredient and a suppository base. Suitable suppository bases are for example, natural or synthetic triglycerides, paraffin hydrocarbons, polyethylene glycols or higher alkanols.

For parenteral administration, aqueous solutions of an active ingredient in water-soluble form, for example of a water-soluble salt, or aqueous injection suspensions that contain viscosity-increasing substances, for example sodium carboxymethylcellulose, sorbitol and/or dextran, and, if desired, stabilizers, are especially suitable. The active ingredient, optionally together with excipients, can also be in the form of a lyophilizate and can be made into a solution before parenteral administration by the addition of suitable solvents.

Solutions such as are used, for example, for parenteral administration can also be employed as infusion solutions.

Preferred preservatives are, for example, antibxidants, such as ascorbic acid, or microbicides, such as sorbic acid or benzoic acid.

The invention relates likewise to a process or a method for the treatment of one of the pathological conditions mentioned hereinabove, especially a disease which responds to an inhibiton of the VEGF-receptor tyrosine kinase or an inhibition of angiogenesis, especially a corresponding neoplastic disease or also psoriasis. The compounds of formula I or N-oxides thereof can be administered as such or especially in the form of pharmaceutical compositions, prophylactically or therapeutically, preferably in an amount effective against the said diseases, to a warm-blooded animal, for example a human, requiring such treatment. In the case of an individual having a bodyweight of about 70 kg the daily dose administered is from approximately 0.05 g to approximately 5 g, preferably from approximately 0.25 g to approximately 1.5 g, of a compound of the present invention.

The present invention relates especially also to the use of a compound of formula I or N-oxides thereof, or a pharmaceutically acceptable salt thereof, especially a compound of formula I which is said to be preferred, or a pharmaceutically acceptable salt thereof, as such or in the form of a pharmaceutical formulation with at least one pharmaceutically acceptable carrier for the therapeutic and also prophylactic management of one or more of the diseases mentioned hereinabove, preferably a disease which responds to an inhibition of VEGF-receptor tyrosine kinase or an inhibition of angiogenesis, especially a neoplastic disease or also psoriasis, more especially if the said disease responds to an inhibition of VEGF-receptor tyrosine kinase or angiogenesis.

The preferred dose quantity, composition, and preparation of pharmaceutical formulations (medicines) which are to be used in each case are described above.

Starting Materials

New starting materials and/or intermediates, as well as processes for the preparation thereof, are likewise the subject of this invention. In the preferred embodiment, such starting materials are used and reaction conditions so selected as to enable the preferred compounds to be obtained.

Starting materials of the formula If and III are known, commercially available, or can be synthesized in analogy to or according to methods that are known in the art.

For example, a pyridine derivative of formula II can be obtained by reaction of a compound of formula VI,

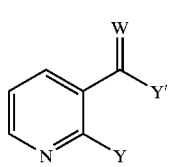

(VI)

wherein W has the meaning as given under formula I, Y is halogen, preferably chloro, and Y' is a leaving group, e.g. alkylthio, azide or preferably halogen, e.g. chloro, with a compound of formula VII,

$R_1$—NH—$R_2$ (VII)

wherein the radicals $R_1$ and $R_2$ have the meaning as given above for formula I. The temperature is preferably carefully controlled in the course of the reaction by cooling or dilution of the reaction mixture and kept between 0° C. and room temperature. Optionally, aqueous alkali is added to combine with the protonated leaving group, e.g. HCl. The reaction is, for example, carried out by adding the amine of formula VII in an inert solvent, like ethyl acetate, ethanol, dimethylformamide or tetrahydrofuran, to an aqueous solution of alkali, for example a solution of sodium hydroxide, potassium hydroxide, sodium hydrogencarbonate or potassium carbonate and optionally catalytic amounts of 4-(dimethylamino) pyridine, and further adding the compound of formula VI in the same or another inert solvent dropwise to the alkaline solution of the amine VII.

All remaining starting materials of are known, capable of being prepared according to known processes, or commercially obtainable; in particular, they can be prepared using processes as described in the Examples.

In the preparation of starting materials, existing functional groups which do not participate in the reaction should, if necessary, be protected. Preferred protecting groups, their introduction and their removal are described under "protecting groups" or in the Examples.

The following Examples serve to illustrate the invention without limiting the invention in its scope.

Temperatures are measured in degrees celsius (° C.). Unless otherwise indicated, the reactions take place at room temperature.

A) PREPARATION OF INTERMEDIATES

Intermediate 1a

2-Chloro-N-(3-trifluoromethylphenyl)-3-pyridinecarboxamide

A solution of 3-aminobenzotrifluoride (Ruka, Buchs, Switzerland; 2.5 mL, 2.90 g, 18 mmol) in ethyl acetate (40 mL) is added to a stirred aqueous solution of sodium hydroxide (40 mL of 1 M, at room temperature. This stirred solution is then treated dropwise over 30 minutes with a solution of 2-chloronicotinoyl chloride (Lancaster Synthesis, Lancashire, England; 3.52 g, 20 mmol) in dry ethyl acetate (25 mL). The resulting mixture is then stirred for 2 h at ambient temperature. The mixture is then extracted with ethyl acetate (3×100 mL) and the combined extracts are sequentially washed with water (2×100 mL), hydrochloric acid (2×100 mL of 2M), water (2×100 mL), saturated aqueous sodium hydrogen carbonate solution (2×100 mL) and saturated aqueous sodium chloride (1×100 mL), dried ($Na_2SO_4$), filtered and the solvent is evaporated off under reduced pressure to yield the crude product which is purified by recrystallisation from ethyl acetate-hexane to give the title compound as a colourless crystalline solid, m.p. 117–118° C.

The following compounds are prepared analogously by utilising the appropriate amine (the supplier of which is e.g. Fluka or Aldrich, both Buchs, Switzerland, or mentioned in parenthesis):

Intermediate 1b: 2-Chloro-N-(4-bromo 3-trifluoromethylphenyl)-3-pyridinecarboxamide, m.p. 173–174° C., utilising 4-bromo-3-trifluoromethylaniline Intermediate 1c: 2-Chloro-N-(3,4-bis(trifluoromethyl) phenyl]-3-pyridinecarboxamide, m.p. 167–169° C., utilising 3,4-bis(trifluoromethyl)aniline (Fluorochem, Derbyshire, England)

Intermediate 1d: 2-Chloro-N-(3-fluoro-5-trifluoromethylphenyl)-3-pyridinecarboxamide, utilising 3-fluoro-5-triluoromethylaniline (Fluorochem, Derbyshire, England)

Intermediate 1e: 2-Chloro-N-(trans-4-tert-butyl-clohexyl)-3-pyridinecarboxamide, m.p. 135–136° C., utilising trans-4-tert-butyl-cyclohexylamine (Lancaster Synthesis, Lancashire, England)

Intermediate 1f: 2-Chloro-N(cis-4-tert-butyl-cyclohexyl)-3-pyridinecarboxamide, m.p. 171–173° C., utilising cis-4-tert-butyl-cyclohexylamine (Lancaster Synthesis, Lancashire, England)

Intermediate 1g: 2-Chloro-N-(4-propylphenyl)-3-pyridinecarboxamide, m.p. 107–110° C., utilising 4-n-propylaniline Intermediate 1h: 2-Chloro-N-(4-butylphenyl)-3-pyridinecarboxamide, m.p. 96–98° C., utilising 4-n-butylaniline Intermediate 1i: 2-Chloro-N-(4-pentylphenyl)-3pyridinecarboxamide, m.p. 94–96° C., utilising 4-n-pentylaniline Intermediate 1j: 2-Chloro-N-(5-indazolyl)-3-pyridinecarboxamide, m.p. 233–255° C., utilising 5-aminoindazole Intermediate 1k: 2-Chloro-N-(3-isoquinolinyl)-3-pyridinecarboxamide, m.p. 180° C., utilising 3-aminoisoquinoline (Maybridge Chemical Co. Ltd., England)

Intermediate 1l: 2-Chloro-N-(4-fluoro-3-trifluoromethylphenyl)-3-pyridinecarboxamide, m.p. 140–141° C., utilising 4-fluoro-3-trifluoromethylaniline Intermediate 1m: 2-Chloro-N-[4-(1,1-dimethylethyl) phenyl]-3-pyridinecarboxamide, m.p. 74–76° C., utilising 4-t-butylaniline Intermediate 1n: 2-Chloro-N-[3-(1,1-dimethylethyl) phenyl]-3-pyridinecarboxamide, utilising 3-t-butylaniline (Maybridge Chemical Co. Ltd., England)

Intermediate 1o: 2-Chloro-N-(2-fluoro-3-trifluoromethylphenyl)-3-pynidinecarboxamide, m.p. 104–105° C., utilising 2-fluoro-3-trifluoromethylaniline Intermediate 1p: 2-Chloro-N-(2-methyl-3-trifluoromethylphenyl)-3-pyridinecarboxamide, m.p. 142–143° C., utilising 2-methyl-3-trifluoromethylaniline (Fluorochem, Derbyshire, England)

Intermediate 1q: 2-Chloro-N-(2-methyl-5-trifluoromethylphenyl)-3-pyridinecarboxamide, m.p. 182–183° C., utilising 2-methyl-5-trifluoromethylaniline (Fluorochem, Derbyshire, England)

Intermediate 2: 2-Chloro-N-[4-(1-propynyl]-3-phenyl)-3-pyridinecarboxamide

A stirred solution of 4-bromoaniline (0.86 g, 5.0 mmol) in dry toluene (50 mL) is purged with argon for 10 minutes. Tributyl-1-propynylstannane. (2.5 g, 6.0 mmol) and tetrakis (triphenylphosphine)palladium(0) (0.15 g) are then added and the resulting mixture is heated at 100° C. for 10 hours under an argon atmosphere. The mixture is cooled, filtered and the solvent is evaporated off under reduced pressure to give crude 4d1-propynyl)benzenamine as an oil. The oil is dissolved in ethyl acetate (15 mL) is added to a stirred aqueous solution of sodium hydroxide (12 mL of 1 M), at room temperature. This stirred solution is then treated dropwise over 30 minutes with a solution of 2-chloronicotinoyl chloride (Lancaster Synthesis, Lancashire, England; 1.06 g, 6 mmol) in dry ethyl acetate (20 mL). The resulting mixture is then stirred for 2 h at ambient temperature. The mixture is then extracted with ethyl acetate (3×50 mL) and the combined extracts are sequentially washed with water (2×40 mL), saturated aqueous sodium hydrogen carbonate solution (2×40 mL) and saturated aqueous sodium chloride (1×40 mL), dried ($Na_2SO_4$), filtered and the solvent is evaporated off under reduced pressure to yield the crude product which is purified by column chromatography on silica gel, eluent 50% ethyl acetate in hexane and recrystallised from ether-hexane to give the title compound as a beige crystalline solid, m.p. 136–138° C.

B) EXAMPLES

Example 1

2-[[2-(4Pyridyl)ethyl]amino]-N-[3-(trifluoromethyl)phenyl]-3-pyridinecarboxamide 4-Pyridineethanamine (Maybridge Chemical Co, Cornwall, England; 0.31 g, 2.5 mmol) is added to a stirred mixture of 2-chloro-N-[3(trifluoromethyl)phenyl]-3-pyridinecarboxamide (intermediate 1a; 0.90 g, 3 mmol), powdered potassium carbonate (0.35 g, 2.5 mmol) and copper(1)iodide; 0.48 g, 2.5 mmol) in dimethylformamide (10 mL). The resulting mixture is then purged with argon and subsequently heated at 100° C. under an argon atmosphere for 2 hours. The mixture is cooled, treated with water (100 mL) and extracted with ethyl acetate (3×80 mL). The combined extracts are washed with an aqueous solution of ammonia (2×50 mL of 10%), dried ($Na_2SO_4$), filtered and the solvent is evaporated off under reduced pressure to yield the crude product which is purified by column chromatography on silica gel, eluent ethyl acetate and recrystalised from ethyl acetate—hexane to give the title compound as a colourless crystalline solid, m.p. 128–138° C.

Example 2

2-[(4-Pyridyl)methylamino]-N-[3-(trifluoromethyl)phenyl]-3-pyridinecarboxamide

A mixture of intermediate 1a (6.00 g, 20 mmol) and 4-pyridinemethanamine (30 mL) is stirred at 150° C. for 16 hours under an argon atmosphere. The cooled mixture is diluted with ethyl acetate (100 mL) and extracted with a saturated aqueous solution of sodium hydrogen carbonate (100 mL), followed by water (4×50 mL) and saturated aqueous sodium chloride (50 mL). The ethyl acetate solution is dried ($Na_2SO_4$), filtered and the solvent is evaporated off under reduced pressure to yield the crude product which is purified by column chromatography on silica gel, eluent ethyl acetate and recrystallised from 2-propanol—diisopropylether to give the title compound as a colourless crystalline solid, m.p. 152–153° C.

The Compounds of Examples 3–16 are Prepared by a Method Analogous to that Described in Examples 1 and 2, by Utilising the Appropriate Amine and Optionally Further Conventional Preparation Methods (e.g. Demethylation with Trimethylsilyl Iodide)

Example 3: 2-(2-Methyl4-pyridyl)methylamino]-N-[3-(trifluoromethyl)phenyl]-3-pyridinecarboxamide; m.p. 144–142° C.

Example 4: (a) 2-[(6-Methoxypyrid-3-yl)methylamino]-N-[3-(trifluoromethyl)phenyl]-3-pyridinecarboxamide; m.p. 89–90° C.

(b) 2-[(6-Methoxypyrid-3-yl)methylamino]-N-[3-(trifluoromethyl)phenyl]-3-pyridine-carboxamide dihydrochloride; m.p. 185° C.

Example 5: 2-[(3Methoxyphenyl)methylamino]-N-[3-(trifluoromethyl)phenyl]-3-pyridinecarboxamide Example 6: 2-[(4-Pyridyl)methylamino]-N-[3,4-bis(trifluoromethyl)phenyl]-3-pyridinecarboxamide; m.p. 194–196° C.

Example 7: 2-[(4-Pyridyl)methylamino]-N-[3-fluoro-5-(trifluoromethyl)phenyl]-3-pyridinecarboxamide, m.p. 196–196° C.

Example 8: 2-[(4-Pyridyl)methylamino]-N-(trans-4-tert-butyl-cyclohexyl)-3-pyridinecarboxamide, m.p. 165–167° C.

Example 9: 2-[(4-Pyridyl)methylamino]-N-[4-(n-propyl)phenyl]-3-pyridinecarboxamide, m.p. 147–149° C.

Example 10: 2-[(4-Pyridyl)methylamino]-N-[4-(n-butyl)phenyl)3-pyridinecarboxamide, m.p. 107–108"C.

Example 11: 2-[(4-Pyridyl)methylamino]-N-[4-(n-pentyl)phenyl]-3-pyridinecarboxamide, m.p. 106–107° C.

Example 12: 2-[(4-Pyridyl)methylamino]-N-[4-(1-propynyl)phenyl]-3-pyridinecarboxamide, m.p. 216–221° C.

Example 13: 2-[(4-Pyridyl)methylamino]-N-(5-indazolyl)-3-pyridinecarboxamide, m.p. 225–230° C.

Example 14: 2-[(4-Pyridyl)methylamino]-N-(3-isoquinolinyl)-3-pyridinecarboxamide, m.p. 191–195° C.

Example 15: 2-(Phenylmethylamino)-N-[3-(trifluoromethyl)phenyl]-3-pyridinecarboxamde, hydrochloride, m.p. 203–207° C. Example 16: 2-[(4-Pyridyl)methylamino]-N-[4-fluoro-3-(trifluoromethyl)phenyl]-3-pyridinecarboxamide, m.p. 172–173° C.

Example 17: 2-[(4-Pyridyl)methylamino]-N[4-(tert-butyl)phenyl]-3-pyridinecarboxamide, m.p. 186–187° C.

Example 18: 2-[(4-Pyridyl)methylamino]-N-[3-((tert-butylethyl)phenyl-3-pyridinecarboxamide, m.p.162–163° C.

Example 19: 2-[(4-Pyridyl)methylamino]-N-[2-fluoro-3-(trifluoromethyl)phenyl]-3-pyridinecarboxamide, m.p. 137–140° C.

Example 20: 2-[(4-Pyridyl)methylamino]-N-[4-bromo-3-(trifluoromethyl)phenyl]-3-pyridinecarboxamide, m.p. 164–165° C.

Example 21: 2-[(4-Pyridyl)methylamino]-N-[2-methyl-3-(trifluoromethyl)phenyl]-3-pyridinecarboxamide, m.p. 146–147° C.

Example 22: 2-[(4-Pyridyl)methylamino]-N-[2-methyl-5-(trifluoromethyl)phenyl]-3-pyridinecarboxamide, m.p. 155–156° C.

Example 23: 2-[(4-Pyridyl)methylamino]-N-(cis-4-tert-butyl-cyclohexyl)-3-pyridinecarboxamide, m.p. 103–106° C.

Example 24: 2-[(6-Methoxypyrid-3-yl)methylamino]-N-[4-bromo-3-(trifluoromethyl)phenyl]-3-pyridinecarboxamide; m.p. 123–125° C.

Example 25: 2-[(6-Methoxypyrid3-yl)methylamino]-N-[2-fluoro-3-trifluoromethyl)phenyl-3-pyridinecarboxamide; m.p. 107–108° C.

Example 26: 2-[(6-Methoxypyrid-3-yl)methylamino]-N-[2-methyl-3-(trifluoromethyl)phenyl-3-pyridinecarboxamide; m.p. 144–146° C.

Example 27: 2-[(1-Oxo-4pyridyl)methylamino]-N-[3-(trifluoromethyl)phenyl]-3-pyridinecarboxamide; m.p. 169–171° C.

Example 28: 2-[3-(N-methyl-carboxamido)phenyl]methylamino]-N-[3-(trifluoromethyl)phenyl]3-pyridinecarboxamide A mixture of 2-amino-N-(3-trifluoromethylphenyl)-3-pyridinecarboxamide (0.56 g, 2.0 mmol), 3-formyl-N-methylbenzamide (0.50 g, 2.4 mmol) and acetic acid (0.5 mL) in methanol (50 mL) is stirred at 25° C. under an argon atmosphere for 12 hours. Sodium cyanoborohyddde (0.40 g of 90%, 5.75 mmol) is added in portions over 30 minutes and the mixture is stirred for 8 hours, then diluted with dichloromethane (100 mL) and treated with a saturated aqueous solution of sodium hydrogen carbonate (50 mL). The mixture is stirred for an additional 5 minutes and filtered to yield the crude product which is purified by crystallisation from isopropanol to give the title compound as a colourless crystalline solid, m.p. 208–210° C.

Example 29

2-[(1-Methyl-pyridin-2(1H)-on-5-yl)methylamino]N-3-(trifluoromethyl)phenyl]-3-pyridinecarboxamide 2-[(6-Methoxypyrid-3-yl)methylamino]-N-[3-(trifluoromethyl)phenyl]-3-pyridinecarboxamide is heated at 140° C. for 18 hours to yield the crude product which is purified by column chromatography on silica gel, eluent 10% ethanol in dichloromethane and and recrystallised from ethylacetate to give the title compound as a beige crystalline solid, m.p. 224–225° C.

Example 30

2-[(6-Methoxypyrid-3-yl)methylamino]-N-[4-propynyl-3-(trifluoromethyl)phenyl]-3-pyridinecarboxamide A stirred solution of 2-[(6-Methoxypyrid-3-yl)methylamino]-N-[4-bromo-3-(trifluoromethyl)phenyl]-3-pyridinecarboxamide (Example 24; 0.96 g, 2.0 mmol) in dry toluene (50 mL) is purged with argon for 20 minutes at 40° C. Tributyl-l-propynylstannane (1.0 g, 2.4 mmol) and tetrakis-(triphenylphosphine)palladium (0) (60 mg) are then added and the resulting mixture is heated at 100° C. for 30 hours under an argon atmosphere. The mixture is then cooled, treated with an aqueous solution of sodium hydroxide (20 mL of 0.1 M) and purged with air for 2 hours. The resulting mixture is then diluted with ethylacetate (200 mL). The orgainic phase is then sequentially washed with water (2×40 mL) and saturated aqueous sodium chloride (1×40 mL), dried ($Na_2SO_4$), filtered and the solvent is evaporated off under reduced pressure to yield the crude product which is purified by column chromatography on silica gel, eluent 50% ethyl acetate in hexane and recrystallised from ether-hexane to give the tite compound as a pale-yellow crystalline solid, m.p. 109–111° C.

The Compounds of Examples 31–32 are Prepared by a Method Analogous to that Described in Example 30 by Utilising the Appropriate Arylbromide Example 31: 2-[(4-Pyridyl)methylamino]-N-[4-propynyl-3-(trifluoromethyl)phenyl]3-pyridinecarboxamide; m.p. 213–217° C. utilising 2-[(4-pyridyl)methylamino]-N-[4-bromo-3-(trifluoromethyl)phenyl]-3-pyndinecarboxamide (Example 20).

Example 32: 2-[(Pyridin-2(1H)-on-5-yl)methyl]amino-N-[4-propynyl-3-(trifluoromethyl)phenyl]-3-pyridinecarboxamide; m.p. 211–218° C. utilising 2-[pyridin-2(1H)-on-5-yl)methyl]amino-N-4-bromo-3-(trifluoromethyl)phenyl]-3-pyridinecarboxamide (Example 35).

Example 33

2-[(Pyridin-2(1H)-on-5-yl)methyl]amino-N-[3 (trifluoromethyl)phenyl]-3-pyridinecarboxamide A mixture of 2-[(6-Methoxypyrid-3-yl)methylamino]-N-[3-(trifluoromethyl)phenyl]-3-pyridinecarboxamide (Example 4; 1.4 g, 3.65 mmol) and trimethylsilyl iodide (Fluka, Buchs, Switzerland; 1.4 mL, 10.3 mmol) in chloroform (30 mL) is stirred at 60° C. for 28 hours. The cooled mixture is then treated with methanol (2 mL) and stirred at room temperature for 10 minutes. The solvent is evaporated off under reduced pressure and the residue is treated with an aqueous solution of ammonia (100 mL of 10%) and extracted with ethyl acetate (3×100 mL). The combined extracts are washed with saturated aqueous sodium chloride (50 mL), dried ($Na_2SO_4$), filtered and the solvent is evaporated off under reduced pressure to yield the crude product which is purified by recrystallisation from hot ethyl acetate to give the title compound as a colourless crystalline solid, ma.p. 200–202° C.

The Compounds of Examples 34–38 are Prepared by a Method Analogous to that Described in Example 33 by Utilising the Appropriate Methoxypyridine Example 34: 2-[(3-Hydroxyphenyl)methyl]amino-N-[3-(trifluoromethyl)phenyl]-3-pyridinecarboxamide; m.p. 143–146° C. by utilising 2-[(3-methoxyphenyl)methylamino]-N-[3-(trifluoromethyl)phenyl]-3-pyridinecarboxamide (Example 5)

Example 35: 2-[(Pyridin-2(1H)-on-5-yl)methyl]amino-N-[4-bromo-3-(trifluoromethyl)phenyl]-3-pyridinecarboxamide; m.p. 202–205° C. by utilising 2-[(6-methoxypyrid-3-yl)methylamino]-N-[4-bromo-3-(trifluoromethyl)phenyl]-3-pyridinecarboxamide (Example 24)

Example 36: 2-[(Pyridin-2(1H)-on-5-yl)methyl]amino-N-[2-fluoro-3-(trifluoromethyl)phenyl]-3-pyridinecarboxamide; m.p. 219–222° C. by utilising 2-[(6-methoxypyrid-3-yl)methylamino]-N-[2-fluoro-3-(trifluoromethyl)phenyl]-3-pyridinecarboxamide (Example 25)

Example 37: 2-[(Pyridin-2-(1H)-on-5-yl)methyl]amino-N-[2-methyl-3-(trifluoromethyl)phenyl]-3-pyridinecarboxamide; m.p. 196–201° C. by utilising 2-[(6-methoxypyrid-3-yl)methylamino]-N-2-methyl-3-trifluoromethyl)phenyl]-3-pyridinecarboxamide (Example 26)

Example 38: 2-[(Pyridin-2(1H)-on-5-yl)methyl]amino-N-[4-propyl-3-(trifluoromethyl)phenyl]-3-pyridinecarboxamide; m.p. 220–224° C. by utilising 2-[(6-methoxypyrid-3-yl)methylamino]-N-[4-propyl-3-(trifluoromethyl)phenyl]-3-pyridinecarboxamide (Example 39)

Example 39

2-[(6-Methoxypyrid-3-yl)methylamino]-N-[4-propyl-3-(trifluoromethyl)phenyl]-3-pyridinecarboxamide A solution of 2-[(6-methoxypyrid-3-yl)methylamino]-N-[4-propynyl-3-(trifluoromethyl)phenyl]-3- pyridinecarboxamide (Example 30; 1.87 g, 4.25 mmol) in methanol (100 mL) is hydrogenated at atmospheric pressure over 5% platinum on carbon (0.4 g) at 22° C. The calculated amount of hydrogen is taken up in 13 hours. The mixture is then filtered and the solvent is evaporated off under reduced pressure to yield the crude product which is purified by recrystallisation from dichloromethane—hexane to give the title compound as a colourless crystalline solid, m.p. 51–61° C.

Example 40

2-[(4-Pyridyl)methyl]amino-N-[4-(n-propyl)-3-(trifluoromethyl)phenyl]-3-pyridinecarboxamide; m.p. 147–149° C. is Obtained Analogously to Example 39, Utilising 2-[(4-Pyridyl)methylamino]-N-[4-propynyl-3-(trifluoromethyl)phenyl]-3-pyridinecarboxamide (Example 31)

Example 41

The following compounds can be obtained according to the procedures described above:

Example 41a: 2-[(4-Pyridyl)methyl]amino-N-(5-thiazolyl)-3-pyridinecarboxamide

Example 41b: 2-[(4-Hydroxyphenyl)methyl]amino-N-[3-(trifluoromethyl)phenyl]-3-pyridinecarboxamide Example 41c: 2-[(4-Pyridyl)methyl]amino-N-(benzo[d]pyrazol-5-yl)-3-pyridinecarboxamide Example 41d: 2-[(6-Methoxy-3-pyridyl)methyl]amino-N-(3-isoquinolinyl)-3-pyridinecarboxamide Example 41e: 2-[(6-Methoxy-3-pyridyl)methyl]amino-N-(benzo[d]pyrazol-5-yl)-3-pyridinecarboxamide Example 41f: 2-[(Pyridin-2(1H)-on-5-yl)methyl]amino-N-(3-isoquinolinyl)-3-pyridinecarboxamide Example 41g: 2-[(Pyridin-2(1H)-on-5-yl)methyl]amino-N-(benzo[d]pyrazol-5-yl)-3-pyridinecarboxamide Example 41h: 2-[(Pyridin-2(1H)-on-5-yl)methyl]amino-N-(cis-4-tert-butyl-cyclohexyl)-3-pyridinecarboxamide Example 41i: 2-[(Pyridin-2(1H)-on-5-yl)methyl]amino-N-(trans-4-tert-butyl-cyclohexyl)-3-pyridinecarboxamide Example 41j: 2-[(1-Oxido-4-pyridyl)methylamino]-N-[4-propyl-3-(trifluoromethyl)phenyl]-3-pyridinecarboxamide Example 41k: 2-[(Pyridin-2(1H)-on-5-yl)methyl]amino-N-[4-ethyl-3-(trifluoromethyl)phenyl]-3-pyridinecarboxamide Example 41l: 2[Pyridin-2(1H)-on-5-yl)methyl]amino-N-[3,4-bis(trifluoromethyl)phenyl]3-pyridinecarboxamide Example 41m: 2-[(1-Methyl-pyridin-2(1H)-on-5-yl)methylamino-N-[3,4-bis(trifluoromethyl)-phenyl]-3-pyridinecarboxamide

Example 42

Soft Capsules 5000 soft gelatin capsules, each comprising as active ingredient 0.05 g of one of the compounds of formula I mentioned in the preceding Examples, are prepared as follows:

| Composition | |
|---|---|
| Active ingredient | 250 g |
| Lauroglycol | 2 liters |

Preparation process: The pulverized active ingredient is suspended in Lauroglykol® (propylene glycol laurate, Gattefossé S. A., Saint Priest, France) and ground in a wet pulverizer to produce a particle size of about 1 to 3 μm. 0.419 g portions of the mixture are then introduced into soft gelatin capsules using a capsule-filling machine.

What is claimed is:

1. A method for the treatment of a disease which responds to the inhibition of the VEGF-receptor tyrosine kinase, which comprises administering an effective amount of a compound of the formula I

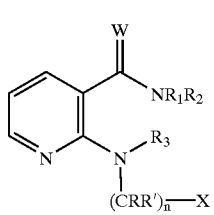

wherein
  n is from 1 up to and including 6;
  W is O or S;
  $R_1$ and $R_3$ represent independently of each other hydrogen, lower alkyl or lower acyl;
  $R_2$ represents a cycloalkyl group, an aryl group, or a mono- or bicyclic heteroaryl group comprising one or more ring nitrogen atoms and 0, 1 or 2 heteroatoms independently from each other selected from the group consisting of oxygen and sulfur, which groups in each case are unsubstituted or mono- or polysubstituted;
  R and R' are independently of each other hydrogen or lower alkyl;
  X represents an aryl group, or a mono- or bicyclic heteroaryl group comprising one or more ring nitrogen atoms and 0, 1 or 2 heteroatoms independently from each other selected from the group consisting of oxygen and sulfur, wherein the term "mono- or bicyclic heteroaryl group" includes, but is not restricted to, a (1H) 2-one-pyridinyl radical, and which groups in each case are unsubstituted or mono- or polysubstituted;
  or of a N-oxide or a possible tautomer thereof;
  or of a pharmaceutically acceptable salt thereof; to a warm-blooded animal requiring such treatment.

2. A method according to claim 1,
wherein
  n is from 1 up to and including 6;
  W is O or S;
  $R_1$ and $R_3$ represent independently of each other hydrogen, lower alkyl or lower acyl;
  $R_2$ represents a cycloalkyl group, an aryl group, or a mono- or bicyclic heteroaryl group comprising one or more ring nitrogen atoms and 0, 1 or 2 heteroatoms independently from each other selected from the group consisting of oxygen and sulfur, which groups in each case are unsubstituted or substituted by up to three substituents, selected from amino, mono- or disubstituted amino, halogen, lower alkyl, substituted alkyl, lower alkenyl, lower alkynyl, lower alkanoyl, hydroxy, etherified or esterified hydroxy, nitro, cyano, carboxy, esterified carboxy, alkanoyl, benzoyl, carbamoyl, N-mono- or N,N-disubstituted carbamoyl, amidino, guanidino, ureido, mercapto, sulfo, lower alkylthio, phenyl, phenoxy, phenylthio, phenyl-lower alkylthio, alkylphenylthio, lower alkylsulfinyl, phenylsulfinyl, phenyl-lower alkylsulfinyl, alkylphenylsulfinyl, lower alkanesulfonyl, phenylsulfonyl, phenyl-lower alkylsulfonyl, alkylphenylsulfonyl, halogen-lower alkylmercapto, halogen-lower alkylsulfonyl, dihydroxybora (—B(OH)$_2$), heterocyclyl, and lower alkylene dioxy bound at adjacent C-atoms of the ring;

R and R' are independently of each other hydrogen or lower alkyl;

X represents an aryl group, or a mono- or bicyclic heteroaryl group comprising one or more ring nitrogen atoms and 0, 1 or 2 heteroatoms independently from each other selected from the group consisting of oxygen and sulfur, wherein the term "mono- or bicyclic heteroaryl group" includes, but is not restricted to, a (1H) 2-one-pyridinyl radical, and which groups in each case are unsubstituted or substituted by up to three substituents, selected from amino, mono- or disubstituted amino, halogen, lower alkyl, substituted alkyl, lower alkenyl, lower alkynyl, lower alkanoyl, hydroxy, etherified or esterified hydroxy, nitro, cyano, carboxy, esterified carboxy, alkanoyl, benzoyl, carbamoyl, N-mono- or N,N-disubstituted carbamoyl, amidino, guanidino, ureido, mercapto, sulfo, lower alkylthio, phenyl, phenoxy, phenylthio, phenyl-lower alkylthio, alkylphenylthio, lower alkylsulfinyl, phenylsulfinyl, phenyl-lower alkylsulfinyl, alkylphenylsulfinyl, lower alkanesulfonyl, phenylsulfonyl, phenyl-lower alkylsulfonyl, alkylphenylsulfonyl, halogen-lower alkylmercapto, halogen-lower alkylsulfonyl, dihydroxybora (—B(OH)$_2$), heterocyclyl, and lower alkylene dioxy bound at adjacent C-atoms of the ring;

or of a N-oxide or a possible tautomer thereof;

or of a pharmaceutically acceptable salt thereof.

3. A method according to claim 1 wherein n is from 1 up to and including 3;

W is O or S;

$R_1$ and $R_3$ represent independently of each other hydrogen, lower alkyl or lower acyl;

$R_2$ represents cyclohexyl, phenyl, indazolyl, thiazolyl, benzo[d]thiazolyl, benzo[d]pyrazolyl or isoquinolinyl, which in each case is unsubstituted or mono- or disubstituted by lower alkyl, lower alkenyl or lower alkynyl; and wherein each radical $R_2$ can be unsubstituted or mono- or polysubstituted with halogen;

R and R' are independently from each other hydrogen or lower alkyl;

X represents phenyl, pyridyl, pyrimidyl or quinolyl, which in each case is unsubstituted or mono- or polysubstituted by oxo, hydroxy, lower alkyl or lower alkoxy;

or a N-oxide or a possible tautomer thereof;

or of a pharmaceutically acceptable salt thereof.

4. A method according to claim 1 wherein n is 1 or 2;

W is O;

$R_1$ and $R_3$ represent hydrogen;

$R_2$ represents cyclohexyl, phenyl, indazolyl, thiazolyl or isoquinolinyl, which in each case is unsubstituted or mono- or disubstituted by lower alkyl or lower alkynyl; and wherein each radical $R_2$ can be unsubstituted or mono- or polysubstituted with halogen;

R and R' are independently from each other hydrogen or lower alkyl;

X represents phenyl, pyridyl, pyrimidyl or quinolyl, which in each case is unsubstituted or mono- or polysubstituted by oxo, hydroxy, lower alkyl or lower alkoxy;

or a N-oxide or a possible tautomer thereof;

or of a pharmaceutically acceptable salt thereof.

5. A method according to claim 1 wherein the disease is a neoplastic disease.

6. A method according to claim 1 wherein the disease is retinopathy or age-related macular degeneration.

7. A compound of the formula I,

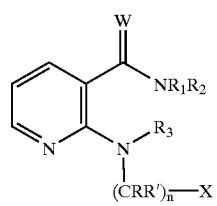

(I)

wherein n is from 1 up to and including 6;

W is O or S;

$R_1$ and $R_3$ represent independently of each other hydrogen, lower alkyl or lower acyl;

$R_2$ represents an cycloalkyl group, an aryl group, or a mono- or bicyclic heteroaryl group comprising one or more ring nitrogen atoms and 0, 1 or 2 heteroatoms independently from each other selected from the group consisting of oxygen and sulfur, wherein the term "mono- or bicyclic heteroaryl group" includes, but is not restricted to, a (1H) 2-one-pyridinyl radical, and which groups in each case are unsubstituted or mono- or polysubstituted;

R and R' are independently of each other hydrogen or lower alkyl;

X represents an aryl group, or a mono- or bicyclic heteroaryl group comprising one or more ring nitrogen atoms and 0, 1 or 2 heteroatoms independently from each other selected from the group consisting of oxygen and sulfur, which groups in each case are unsubstituted or mono- or polysubstituted;

or a N-oxide or a possible tautomer thereof;

or a pharmaceutically acceptable salt of such a compound;

with the exception of the compounds of formula I wherein n is 1, W is O, $R_1$, $R_3$, R, R' are hydrogen, X is phenyl and $R_2$ is 3-trifluoromethylphenyl, 2-methoxyphenyl or 2-chloro-3-pyridyl, or X is 4-methoxyphenyl and $R_2$ is 2-chloro-3-pyridyl or X is 4-pyridyl and $R_2$ is 4-[3-(3-pyridyl)-5-trifluoromethyl-pyrazol-1-yl]-phenyl, and the compound of formula I wherein n is 1, W is O, $R_3$, R, R' are hydrogen, $R_1$ is methyl, $R_2$ is 2-chloro-3-pyridyl and X is phenyl.

8. A compound of the formula I,

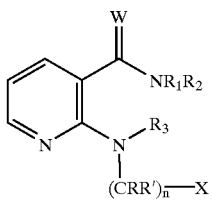

(I)

wherein n is from 1 up to and including 6;

W is O or S;

$R_1$ and $R_3$ represent independently of each other hydrogen, lower alkyl or lower acyl;

$R_2$ represents an cycloalkyl group, an aryl group, or a mono- or bicyclic heteroaryl group comprising one or more ring nitrogen atoms and 0, 1 or 2 heteroatoms independently from each other selected from the group consisting of oxygen and sulfur, wherein the term mono- or bicyclic heteroaryl group" includes, but is not restricted to, a (1H) 2-one-pyridinyl radical, and which groups in each case are unsubstituted or mono- or polysubstituted;

R and R' are independently of each other hydrogen or lower alkyl;

X represents an aryl group, or a mono- or bicyclic heteroaryl group comprising one or more ring nitrogen atoms and 0, 1 or 2 heteroatoms independently from each other selected from the group consisting of oxygen and sulfur, which groups in each case are unsubstituted or mono- or polysubstituted;

or a N-oxide or a possible tautomer thereof;

or a pharmaceutically acceptable salt of such a compound; with the exception of the compounds of formula I wherein n is 1, W is O, $R_1$, $R_3$, R, R' are hydrogen, X is phenyl and $R_2$ is 3-trifluoromethylphenyl, 2-methoxyphenyl or 2-chloro-3-pyridyl, or X is 4-methoxyphenyl and $R_2$ is 2-chloro-3-pyridyl or X is 4-pyridyl and $R_2$ is phenyl substituted in 4-position by unsubstituted or substituted 1-pyrazolyl, and the compound of formula I wherein n is 1, W is O, $R_3$, R, R' are hydrogen, $R_1$ is methyl, $R_2$ is 2-chloro-3-pyridyl and X is phenyl.

9. A compound of the formula I according to claim 7, wherein n is from 1 up to and including 6;

W is O or S;

$R_1$ and $R_3$ represent independently of each other hydrogen, lower alkyl or lower acyl;

$R_2$ represents a cycloalkyl group, an aryl group, or a mono- or bicyclic heteroaryl group comprising one or more ring nitrogen atoms and 0, 1 or 2 heteroatoms independently from each other selected from the group consisting of oxygen and sulfur, which groups in each case are unsubstituted or substituted by up to three substituents, selected from amino, mono- or disubstituted amino, halogen, lower alkyl, substituted alkyl, lower alkenyl, lower alkynyl, lower alkanoyl, hydroxy, etherified or esterified hydroxy, nitro, cyano, carboxy, esterified carboxy, alkanoyl, benzoyl, carbamoyl, N-mono- or N,N-disubstituted carbamoyl, amidino, guanidino, ureido, mercapto, sulfo, lower alkylthio, phenyl, phenoxy, phenylthio, phenyl-lower alkylthio, alkylphenylthio, lower alkylsulfinyl, phenylsulfinyl, phenyl-lower alkylsulfinyl, alkylphenylsulfinyl, lower alkanesulfonyl, phenylsulfonyl, phenyl-lower alkylsulfonyl, alkylphenylsulfonyl, halogen-lower alkylmercapto, halogen-lower alkylsulfonyl, dihydroxybora (—B(OH)$_2$), heterocyclyl, and lower alkylene dioxy bound at adjacent C-atoms of the ring;

R and R' are independently of each other hydrogen or lower alkyl;

X represents an aryl group, or a mono- or bicyclic heteroaryl group comprising one or more ring nitrogen atoms and 0, 1 or 2 heteroatoms independently from each other selected from the group consisting of oxygen and sulfur, wherein the term "mono- or bicyclic heteroaryl group" includes, but is not restricted to, a (1H) 2-one-pyridinyl radical, and which groups in each case are unsubstituted or substituted by up to three substituents, selected from amino, mono- or disubstituted amino, halogen, lower alkyl, substituted alkyl, lower alkenyl, lower alkynyl, lower alkanoyl, hydroxy, etherified or esterified hydroxy, nitro, cyano, carboxy, esterified carboxy, alkanoyl, benzoyl, carbamoyl, N-mono- or N,N-disubstituted carbamoyl, amidino, guanidino, ureido, mercapto, sulfo, lower alkylthio, phenyl, phenoxy, phenylthio, phenyl-lower alkylthio, alkylphenylthio, lower alkylsulfinyl, phenylsulfinyl, phenyl-lower alkylsulfinyl, alkylphenylsulfinyl, lower alkanesulfonyl, phenylsulfonyl, phenyl-lower alkylsulfonyl, alkylphenylsulfonyl, halogen-lower alkylmercapto, halogen-lower alkylsulfonyl, dihydroxybora (—B(OH)$_2$), heterocyclyl, and lower alkylene dioxy bound at adjacent C-atoms of the ring;

or a N-oxide or a possible tautomer thereof;

or a pharmaceutically acceptable salt of such a compound; with the exception of the compounds of formula I wherein n is 1, W is O, $R_1$, $R_3$, R, R' are hydrogen, X is phenyl and $R_2$ is 3-trifluoromethylphenyl, 2-methoxyphenyl or 2-chloro-3-pyridyl, or X is 4-methoxyphenyl and $R_2$ is 2-chloro-3-pyridyl or X is 4-pyridyl and $R_2$ is phenyl substituted in 4-position by unsubstituted or substituted 1-pyrazolyl, and the compound of formula I wherein n is 1, W is O, $R_3$, R, R' are hydrogen, $R_1$ is methyl, $R_2$ is 2-chloro-3-pyridyl and X is phenyl.

10. A compound of the formula I according to claim 7, wherein n is from 1 up to and including 3;

W is 0 or S;

$R_1$ and $R_3$ represent independently of each other hydrogen, lower alkyl or lower acyl;

$R_2$ represents cyclohexyl, phenyl, indazolyl, thiazolyl, benzo[d]thiazolyl, benzo[d]pyrazolyl or isoquinolinyl, which in each case is unsubstituted or mono- or disubstituted by lower alkyl, lower alkenyl or lower alkynyl; and wherein each radical $R_2$ can be unsubstituted or mono- or polysubstituted with halogen;

R and R' are independently from each other hydrogen or lower alkyl;

X represents phenyl, pyridyl, pyrimidyl or quinolyl, which in each case is unsubstituted or mono- or polysubstituted by oxo, hydroxy, lower alkyl, lower alkoxy or N-lower alkyl carbamoyl;

or a N-oxide or a possible tautomer thereof;
or a pharmaceutically acceptable salt of such a compound;
with the exception of the compounds of formula I wherein n is 1, W is O, R₁, R₃, R, R' are hydrogen, X is phenyl and R₂ is 3-trifluoromethylphenyl or 2-methoxyphenyl.

11. A compound of the formula I according to claim 7, wherein n is 1 or 2;
W is O or S;
R₁ and R₃ represent hydrogen;
R₂ represents cyclohexyl, phenyl, indazolyl, thiazolyl or isoquinolinyl, which in each case is unsubstituted or mono- or disubstituted by lower alkyl or lower alkynyl; and wherein each radical R₂ can be unsubstituted or mono- or polysubstituted with halogen;
R and R' are independently from each other hydrogen or lower alkyl;
X represents phenyl, pyridyl, pyrimidyl or quinolyl, which in each case is unsubstituted or mono- or polysubstituted by oxo, hydroxy, lower alkyl, lower alkoxy or N-lower alkyl carbamoyl;
or a N-oxide or a possible tautomer thereof;
or a pharmaceutically acceptable salt of such a compound;
with the exception of the compounds of formula I wherein n is 1, R, R' are hydrogen, X is phenyl and R₂ is 3-trifluoromethylphenyl or 2-methoxyphenyl.

12. A compound of the formula I according to claim 7, selected from the group of compounds consisting of 2-[2-(4-Pyridyl)ethyl]amino-N-[3-(trifluoromethyl)phenyl]-3-pyridinecarboxamide,
2-[(4-Pyridyl)methyl]amino-N-[3-(trifluoromethyl)phenyl]-3-pyridinecarboxamide,
2-[(2-Methyl-4-pyridyl)methyl]amino-N-[3-(trifluoromethyl)phenyl]-3-pyridinecarboxamide,
2-[(6-Methoxy-3-pyridyl)methyl]amino-N-[3-(trifluoromethyl)phenyl]-3-pyridinecarboxamide,
2-[(4-Pyridyl)methyl]amino-N-[3,4-bis(trifluoromethyl)phenyl]-3-pyridinecarboxamide,
2-[(4-Pyridyl)methyl]amino-N-[5-fluoro-3-trifluoromethyl-phenyl]-3-pyridinecarboxamide,
2-[(4-Pyridyl)methyl]amino-N-(trans-4-tert-butyl-cyclohexane)-3-pyridinecarboxamide,
2-[(4-Pyridyl)methyl]amino-N-(4-n-propyl-phenyl)-3-pyridinecarboxamide,
2-[(4-Pyridyl)methyl]amino-N-(4-n-butyl-phenyl)-3-pyridinecarboxamide,
2-[(4-Pyridyl)methyl]amino-N-(4-n-pentyl-phenyl)-3-pyridinecarboxamide,
2-[(4-Pyridyl)methyl]amino-N-[4-(1-propynyl)-phenyl]-3-pyridinecarboxamide,
2-[(4-Pyridyl)methyl]amino-N-(5-indazolyl)-3-pyridinecarboxamide,
2-[(4-Pyridyl)methyl]amino-N-(3-isoquinolinyl)-3-pyridinecarboxamide,
2-[(Pyridin-6(1H)-on-3-yl)methyl]amino-N-[3-(trifluoromethyl)phenyl]-3-pyridinecarboxamide, and the pharmaceutically acceptable salts thereof.

13. A compound of the formula I according to claim 7, selected from the group of compounds consisting of 2-(Phenylmethylamino)-N-[3-(trifluoromethyl)phenyl]-3-pyridine-carboxamide, hydrochloride,
2-[(4-Pyridyl)methylamino]-N-[2-fluoro-3-(trifluoromethyl)phenyl]-3-pyridinecarboxamide,
2-[(4-Pyridyl)methylamino]-N-[4-bromo-3-(trifluoromethyl)phenyl]-3-pyridinecarboxamide,
2-[(4-Pyridyl)methylamino]-N-[2-methyl-3-(trifluoromethyl)phenyl]-3-pyridinecarboxamide,
2-[(4-Pyridyl)methylamino]-N-[2-methyl-5-(trifluoromethyl)phenyl]-3-pyridinecarboxamide,
2-[(4-Pyridyl)methylamino]-N-(cis-4-tert-butyl-cyclohexyl)-3-pyridinecarboxamide,
2-[(6-Methoxypyrid-3-yl)methylamino]-N-[4-bromo-3-(trifluoromethyl)phenyl]-3-pyridinecarboxamide,
2-[(6-Methoxypyrid-3-yl)methylamino]-N-[2-fluoro-3-(trifluoromethyl)phenyl]-3-pyridinecarboxamide,
2-[(6-Methoxypyrid-3-yl)methylamino]-N-[2-methyl-3-(trifluoromethyl)phenyl]-3-pyridinecarboxamide,
2-[(1-Oxido-4-pyridyl)methylamino]-N-[3-(trifluoromethyl)phenyl]-3-pyridinecarboxamide,
2-[3-(N-methyl-carboxamido)phenyl]methylamino]-N-[3-(trifluoromethyl)phenyl]-3-pyridinecarboxamide,
2-[(1-Methyl-pyridin-2(1H)-on-5-yl)methylamino]-N-[3-(trifluoromethyl)phenyl]-3-pyridine-carbonoxamide.
2-[(6-Methoxypyrid-3-yl)methylamino]-N-[4-propynyl-3-(trifluoromethyl)phenyl]-3-pyridinecarboxamide,
2-[(4-Pyridyl)methylamino]-N-[4-propynyl-3-(trifluoromethyl)phenyl]-3-pyridinecarboxamide,
2-[(Pyridin-2(1H)-on-5-yl)methyl]amino-N-[4-propynyl-3-(trifluoromethyl)phenyl]-3-pyridinecarboxamide,
2-[(Pyridin-2(1H)-on-5-yl)methyl]amino-N-[3-(trifluoromethyl)phenyl]-3-pyridinecarboxamide,
2-[(3-Hydroxyphenyl)methyl]amino-N-[3-(trifluoromethyl)phenyl]-3-pyridinecarboxamide,
2-[(Pyridin-2(1H)-on-5-yl)methyl]amino-N-[4-bromo-3-(trifluoromethyl)phenyl]-3-pyridinecarboxamide,
2-[(Pyridin-2(1H)-on-5-yl)methyl]amino-N-[2-fluoro-3-(trifluoromethyl)phenyl]-3-pyridinecarboxamide,
2-[(Pyridin-2(1H)-on-5-yl)methyl]amino-N-[2-methyl-3-(trifluoromethyl)phenyl]-3-pyridinecarboxamide,
2-[(Pyridin-2(1H)-on-5-yl)methyl]amino-N-[4-propyl-3-(trifluoromethyl)phenyl]-3-pyridinecarboxamide,
2-[(6-Methoxypyrid-3-yl)methylamino]-N-[4-propyl-3-(trifluoromethyl)phenyl]-3-pyridinecarboxamide,
2-[(4-Pyridyl)methyl]amino-N-[4-(n-propyl)-3-(trifluoromethyl)phenyl]-3-pyridinecarboxamide,
2-[(4-Pyridyl)methyl]amino-N-(5-thiazolyl)-3-pyridinecarboxamide,
2-[(4-Hydroxyphenyl)methyl]amino-N-[3-(trifluoromethyl)phenyl]-3-pyridine-carboxamide,
2-[(4-Pyridyl)methyl]amino-N-(benzo[d]pyrazol-5-yl)-3-pyridinecarboxamide,
2-[(6-Methoxy-3-pyridyl)methyl]amino-N-(3-isoquinolinyl)-3-pyridinecarboxamide,
2-[(6-Methoxy-3-pyridyl)methyl]amino-N-(benzo[d]pyrazol-5-yl)-3-pyridinecarboxamide,
2-[(Pyridin-2(1H)-on-5-yl)methyl]amino-N-(3-isoquinolinyl)-3-pyridinecarboxamide,
2-[(Pyridin-2(1H)-on-5-yl)methyl]amino-N-(benzo[d]pyrazol-5-yl)-3-pyridinecarboxamide,
2-[(Pyridin-2(1H)-on-5-yl)methyl]amino-N-(cis-4-tert-butyl-cyclohexyl)-3-pyridinecarboxamide,
2-[(Pyridin-2(1H)-on-5-yl)methyl]amino-N-(trans-4-tert-butyl-cyclohexyl)-3-pyridinecarboxamide,
2-[(1-Oxido-4-pyridyl)methylamino]-N-[4-propyl-3-(trifluoromethyl)phenyl]-3-pyridinecarboxamide, 2-[(Pyridin-2(1H)-on-5-yl)methyl]amino-N-[4-ethyl-3-(trifluoromethyl)phenyl]-3-pyridinecarboxamide, 2-[(Pyridin-2(1H)-on-5-yl)methyl]amino-N-[3,4-bis(trifluoromethyl)phenyl]-3-pyridinecarboxamide, 2-[(1-Methyl-pyridin-2(1H)-on-5-yl)methylamino]-N-[3,4-bis(trifluoromethyl)-phenyl]-3-pyridinecarboxamide, and the pharmaceutically acceptable salts thereof.

14. A pharmaceutical preparation, comprising a compound of formula I according to claim 7, a tautomer, a N-oxide or a pharmaceutically acceptable salt thereof, or a hydrate or solvate thereof, and at least one pharmaceutically acceptable carrier.

15. A process for the preparation of a compound of formula I according to claim 7, or a N-oxide or a pharmaceutically acceptable salt thereof, characterized in that a pyridine derivative of the formula II

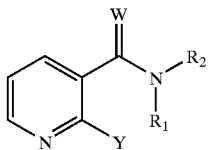

(II)

wherein W, $R_1$ and $R_2$ are as defined for a compound of the formula I and Y is halogen is reacted with an amine of the formula III $$R_3\text{—NH—}(CRR')_n\text{—X} \qquad (III)$$

wherein n, R, R', $R_3$ and X are as defined for a compound of the formula I in the presence of a base and a copper(I) compound optionally in the presence of an inert solvent;

where the above starting compounds II and III may also be present with functional groups in protected form if necessary and/or in the form of salts, provided a salt-forming group is present and the reaction in salt form is possible;

any protecting groups in a protected derivative of a compound of the formula I are removed;

and, if so desired, an obtainable compound of formula I is converted into another compound of formula I or a N-oxide thereof, a free compound of formula I is converted into a salt, an obtainable salt of a compound of formula I is converted into the free compound or another salt, and/or a mixture of isomeric compounds of formula I is separated into the individual isomers.

* * * * *

UNITED STATES PATENT AND TRADEMARK OFFICE
CERTIFICATE OF CORRECTION

PATENT NO. : 6,624,174 B2
DATED : September 23, 2003
INVENTOR(S) : Paul William Manley et al.

It is certified that error appears in the above-identified patent and that said Letters Patent is hereby corrected as shown below:

Column 1,
Line 39, should read -- proteolytic degradation of extracellular matrix during the --

Column 3,
Line 61, should read -- benzoyl, carbamoyl, N-mono or N,N-disubstituted --

Column 5,
Line 5, should read -- in addition to the previous group $C_8^-C_{20}$alkyloxy, such as --

Column 6,
Line 16, should read -- acids, azclaic acid, malic acid, tartaric acid, citric acid, amino --

Column 8,
Line 1, should read -- the PC-3 prostate carcinoma cell line PC-3 (ATCC No. --

Column 9,
Line 7, should read -- In this model, the hyperalgesia caused by an intra-planar yeast --

Column 15,
Line 44, should read -- 2-[(Pyridin-2(1H)-on-5-yl)methyl]amino-N-[2-methyl-3- --
Line 48, should read -- (trifluoromethyl)phenyl]3-pyridinecarboxamide, --

Column 18,
Line 33, should read -- Houben Weyl, $4^{th}$ edition, Volume 15/1, George Thieme --

Column 22,
Line 25, should read -- may comprise excipients, for example preservatives, --

Column 24,
Line 41, should read -- Starting materials of the formula II and II are known, --

Column 25,
Line 34, should read -- A solution of 3-aminobenzotrifluorid Fluka, Buchs, --

Column 26,
Line 18, should read -- 3-pyridinecarboxamide, m.p. 94-96º C., utilising 4-n- --

UNITED STATES PATENT AND TRADEMARK OFFICE
CERTIFICATE OF CORRECTION

PATENT NO. : 6,624,174 B2
DATED : September 23, 2003
INVENTOR(S) : Paul William Manley et al.

It is certified that error appears in the above-identified patent and that said Letters Patent is hereby corrected as shown below:

Column 28,
Line 15, should read -- 195-196º C. --

Column 29,
Line 14, should read -- atmosphere for 12 hours. Sodium cyanoborohydride (0.40 g --

Signed and Sealed this

Tenth Day of August, 2004

JON W. DUDAS
*Acting Director of the United States Patent and Trademark Office*